(12) United States Patent
Weber et al.

(10) Patent No.: US 9,779,206 B2
(45) Date of Patent: Oct. 3, 2017

(54) ESTIMATION OF DELTA-CQ VALUES WITH CONFIDENCE FROM QPCR DATA

(75) Inventors: Karsten Weber, Leverkusen (DE); Inke Sabine Feder, Leverkusen (DE)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 796 days.

(21) Appl. No.: 13/704,655

(22) PCT Filed: May 16, 2011

(86) PCT No.: PCT/EP2011/057863
§ 371 (c)(1),
(2), (4) Date: Dec. 17, 2012

(87) PCT Pub. No.: WO2011/157501
PCT Pub. Date: Dec. 22, 2011

(65) Prior Publication Data
US 2013/0090863 A1 Apr. 11, 2013

(30) Foreign Application Priority Data

Jun. 17, 2010 (EP) .................... 10166256

(51) Int. Cl.
| | | |
|---|---|---|
| G01N 33/48 | (2006.01) | |
| G06F 19/24 | (2011.01) | |
| C12Q 1/68 | (2006.01) | |
| G06F 19/20 | (2011.01) | |
| G01N 33/50 | (2006.01) | |

(52) U.S. Cl.
CPC ........... *G06F 19/24* (2013.01); *C12Q 1/6851* (2013.01); *G06F 19/20* (2013.01)

(58) Field of Classification Search
CPC .................................................... G06F 19/22
See application file for complete search history.

(56) References Cited

FOREIGN PATENT DOCUMENTS

| WO | 00/78991 | 12/2000 |
|---|---|---|
| WO | 2010/003771 | 1/2010 |

OTHER PUBLICATIONS

Schwers Stephan et al: "A high-sensitivity, medium-density, and target amplification-free planar waveguide microarray system for gene expression analysis of formalin-fixed and paraffin-embedded tissue" Clinical Chemistry, American Association of Clinical Chemistry, 55(11): 1995-2003 (2009).
Follestad Turid et al, "A Bayesian Hierarchical Model for Quantitative Real-Time PCR Data", Statistical Applications in Genetics and Molecular Biology, 9(1):1-18, (2010).
Hellemans Jan et al, "qBase relative quantification framework and software for real-time quantitative PCR data" Genome Biology, Biomed Central Ltd., 8(2): R19, (2007).
International Search Report for PCT/EP/2011/057863, dated Sep. 30, 2011.
Livak et al., Analysis of relative gene expression data using real-time quantitative PCR and the $2^\wedge$ -delta delta Ct method, Methods, 25: 402-408, (2001).
Pfaffl, Michael W., A new mathematical model for relative quantification in real-time RT-PCR, Nucleic Acids Research 29 (9):2002-2007, (2001).
Bengtsson et al., Quantification of mRNA in single cells and modelling of RT-qPCR induced noise, BMC Molecular Biology, 9:63 (2008).
Bustin et al., The MIQE Guidelines: Minimum Information for Publication of Quantitative Real-Time PCR Experiments. Clinical Chemistry, 55(4): 611-622, (2009).

*Primary Examiner* — Eric S DeJong

(57) ABSTRACT

The invention describes how to estimate delta-Cq values from measured (raw-)Cq values gained from PCR measurements and how to calculate confidence intervals for them. This is realized by the following processing steps: A noise model, which might be constructed on some training PCR data, calculates the distribution of the true target material concentration of a single well for an observed measurement results. Said distribution is calculated for all types of measurement results including "Numeric" raw-Cq values as well as Cq being "Undetected", which denotes that no fluorescence signal was detected during all cycles and thus corresponds to no or very few target molecules.

21 Claims, 3 Drawing Sheets

ESTIMATION OF DELTA-CQ VALUES WITH CONFIDENCE FROM QPCR DATA

Figure 1:
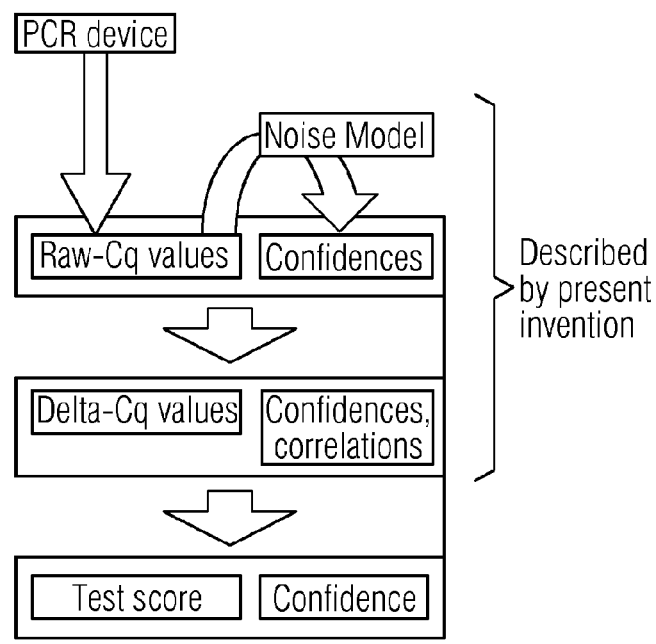

This application claims the benefit of European Patent Application No. EP10166256.7 filed on Jun. 17, 2010, the disclosure of which is incorporated, in its entirety, by this reference.

The invention is in the field of analytic technology and medical diagnostics, in particular and relates to methods and systems for determining measurements from quantitative nucleic acid amplification reactions, such as PCR. In particular, it describes how to estimate delta-Cq values from measured (raw-)Cq values gained from PCR measurements and how to calculate confidence intervals for them.

Quantitative PCR measurements require normalization to a reference to yield expression values that can be compared across samples and/or patients. One possible method for this task is the so-called delta-Cq method (formerly called delta-Ct method), see [1, 2, 4]. Basically, the difference between the (raw-)Cq value of a gene of interest and the average of the (raw-)Cq values of some reference genes is calculated and called delta-Cq value.

The invention describes how to calculate confidence intervals for delta-Cq values gained from PCR measurements on material from a tissue sample. These confidence intervals can be used to determine how precise and/or reliable a test result is and thus can be used to determine whether the test result should be reported or the measurements should be repeated to improve confidence. Said confidence intervals can also be used to calculate probabilities for a gene expression value, biomarker value or multivariate biomarker score to be above a certain threshold and thus improve the decision process of how to treat the patient if one or more treatment options depend on said threshold.

SUMMARY OF THE INVENTION

The invention relates to the method of claim 1 and the System of claim 13. Preferred embodiments are described in the dependent claims.

The Method of claim 1 and the embodiments described in the dependent claims may be implemented with all its features in the system according to the invention.

In particular the invention relates to

1. Method for determining a normalized concentration or activity of an analyte in a sample, including a respective confidence information, the method comprising:
a) determining one or more measurement values representative of the concentration or activity of the analyte from the sample,
b) determining one or more measurement values representative of the concentration or activity of at least one reference substance from said and/or other samples,
c) obtaining an estimation by using an estimator of true or related values and respective confidence information for said estimate for the concentration or activity of the analyte and the at least one reference substance from the measurements in a) and b),
d) obtaining an estimation by using an estimator of a normalized value and respective confidence information for said estimate representative of the concentration or activity of the analyte from values in a), b) and c), wherein the normalized value and respective confidence information is bounded from below, above or both,
wherein the confidence information from d) is used to determine a quality control criterion for said determination of the concentration or activity of the analyte.

2. Method according to count 1, wherein the application of the one or two bounds according to step d) leads to a variance (i.e. reciprocal confidence) of the bounded normalized estimation according to step d) which is smaller than the variance of the estimation of the concentration or activity of the analyte according to step c) for at least one observable measurement value.

Preferentially the variance of the bounded normalized estimation according to step d) for said observable measurement value is not more than four times larger than the median variance of bounded normalized estimations according to step d) in a representative set of samples.

3. Method according to counts 1 or 2, wherein the analyte is a nucleic acid, in particular DNA or RNA, in particular mRNA.

4. Method according to any of the preceding counts, wherein the measurement values are (raw-)Ct values or (raw-)Cq values.

5. Method according to any of the preceding counts, wherein the measurement values a) and b) be one of:
a numeric value related to the concentration or activity or the target or reference, respectively,
the value "Undetected" related to a very small concentration or activity, in particular below the LOD,
the value "Invalid" denoting that a severe problem occurred during measurement and this measurement or replicate should be ignored.

6. Method according to any of the preceding counts, wherein several replicates for the target and/or the references are measured and combined into one normalized value.

7. Method according to count 6, wherein outliers within replicates are eliminated by an automated procedure before step a) and the elimination rule is based on the same or a derived noise model as used in count 1.

8. Method according to counts 1, 2 and 5, wherein in step d) a lower bound is used that is determined on a training data set by constrained optimization (automatically or manually), wherein the lower bound is optimized to be as high as possible to make the variance (i.e. lack of confidence) of bounded normalized values as small as possible, and wherein the constraint depends on the application of normalized values, wherein the lower bound is constrained be so low that for said application no distinction between values at and below the lower bound needs to be made (i.e. there is no loss of information by bounding with respect to said application). The same applies to an upper bound with switched signs for optimization aim and constraint.

9. Method according to any of the preceding counts, wherein step c) of count 1 is realized by a noise model wherein the true value is modeled as a normal distribution with mean equal to the measured value and a standard deviation calculated from a parameterized function, where parameters were fitted based on training data.

10. Method according to any of the counts 1 to 8, wherein step c) of count 1 is realized by a noise model wherein the measured value is modeled as a normal distribution with mean equal to the true value and a standard deviation calculated from a parameterized function, where parameters were fitted based on training data.

Application of this noise model is realized by the Bayesian formula.

11. Method according to count 5 and 9 or 10 wherein whenever "Undetected" is measured, the noise model assigns a fixed distribution to the true value, said distribution having finite or infinite expected value, finite or infinite variance, or bounded or half-bounded or unbounded support.

12. Method of any of the above counts, wherein the quality control criterion is used to make at least one of the following decisions:
  (i) report or reject the estimate
  (ii) repeat or repeat not measurements
  (iii) decide whether the estimate is used for a decision
  (iv) determine whether the normalized value or a combination of normalized values exceeds a threshold 13. System determining a normalized concentration or activity of an analyte in a sample, including a respective confidence information, comprising
  a) means for inputting one or more measurement values representative of the concentration or activity of the analyte from the sample,
  b) means for inputting one or more measurement values representative of the concentration or activity of at least one reference substance from said and/or other samples,
  c) means for obtaining an estimation by using an estimator of true or related values and respective confidence information for said estimate for the concentration or activity of the analyte and the at least one reference substance from the measurements in a) and b),
  d) means for obtaining an estimation by using an estimator of a normalized value and respective confidence information for said estimate representative of the concentration or activity of the analyte from values in a), b) and c), wherein the normalized value is bounded from below, above or both,
  wherein the confidence information from d) is used to determine a quality control criterion for said determination of the concentration or activity of the analyte, and
  wherein said means of (a), (b), (c) and (d) are implemented as a computer program product.

14. System according to count 13, further comprising means for measuring one or more measurement values representative of the concentration or activity of the analyte from the sample.

The invention is realized by the following processing steps: A noise model, which might be constructed on some training PCR data, calculates the distribution of the true target material concentration of a single well for an observed measurement results. Said distribution is calculated for all types of measurement results including "Numeric" raw-Cq values as well as Cq being "Undetected", which denotes that no fluorescence signal was detected during all cycles and thus corresponds to no or very few target molecules. Based on this distribution information from several replicate wells of a gene of interest and several replicate wells of one or more reference genes the distribution of the true delta-Cq value is calculated. In order to come out with a finite variance of the delta-Cq value (which so far would not be the case if all replicates are "Undetected") a lower bound is defined on the delta-Cq value. This lower bound is chosen so small that no useful information about the clinical implications is lost but so large that even for samples with low total material yield a reliable estimation of the delta-Cq value is possible.

Definitions material from a sample: describes any kind of material measurements are performed in or with. The term is not restricted to direct or indirect measurements and it describes the original material as well as extractions of it. Example materials are FFPE breast cancer tissue slides (and eluates from it), fresh-frozen tissue slides, resections gained during surgeries, blood, stool, callus, hairs, spit, leaves, juice, resin and cultured germs.

QPCR: quantitative polymerase chain reaction. The term shall relate to all technical measuring procedures comprising of cycle-based amplification and detection of the amount of amplified substance.

Cq value: quantification cycle of a qPCR as defined by the MIQE guidelines [4]. Examples include the threshold cycle (Ct), the crossing point (Cp) and the adjusted inflexion point (AIP). The Cq value is the measurement result and thus the input into the processing procedure of the present invention.

type of Cq value, type of result, type of measurement result: A measurement (one target, one sample, one replicate) is assumed to result in one of three classes:
  (i) "Numeric" denotes a real-valued (raw-)Cq value which relates to the amount of target material in the sample before amplification. The smaller the (raw-)Cq value the higher the amount of material.
  (ii) "Undetected" denotes that no amplification was detected. This relates to the situation of no or very few target material in the sample.
  (iii) "Invalid" relates to a problem and/or severe doubt associated with this measurement. An "Invalid" Cq value is interpreted as to contain no useful information.

raw-Cq value: Synonym to Cq value; the term raw-Cq value is used to distinguish from delta-Cq values. Raw-Cq values are the input into the procedure describes by the present invention: For each gene of interest and each reference gene there may be several replicate raw-Cq values.

Normalized: Normalization of measurement values shall be understood in a very general meaning. A normalized value is a value calculated from (raw) values that is more related to the chemical behavior or the features of a biological system than the raw values. A raw value may be more related to technical aspects of the sample such as total volume, total RNA or DNA amount, variations in devices and reagents, storage time and conditions, or others.

delta-Cq value: Special instance of normalized measurement value, see [1, 2] for motivation and description. Deviating from this we use a slightly different definition:

$$\text{delta-Cq(GOI)} := 20 - \text{raw-Cq(GOI)} + \text{mean(raw-Cq(reference genes))}$$

The constant 20 was introduced to avoid negative delta-Cq values; the person skilled in the art knows that this constant is arbitrary and does not change the information contained in the calculated results nor its confidence.

The delta-Cq value and its confidence are the output of the procedure describes by the present invention; for one gene of interest and several reference gene one delta-Cq value is calculated.

replicates: one or more measurements of the same gene within the same material of a sample. The present invention can deal with any number of replicates and different numbers of replicates for different genes. Nevertheless two or more replicates for each gene enable the calculation of a delta-Cq even if one replicate results in "Invalid". Three or more replicates enable the automatic detection and removal of outliers within replicates.

gene of interest (GOI): the substance a delta-Cq value shall be measured and calculated. The term shall not be restricted to genes; it shall be understood as any substance being amplifiable or having a quantitatively equivalent derivative that is amplifiable.

target: synonym to gene of interest.

reference gene: the substance or target the GOI may be referenced to. The term shall not be restricted to genes; it shall be understood as any substance being amplifiable or having a quantitatively equivalent derivative that is amplifiable. Referencing is realized by calculation of delta-Cq values respectively calculating the difference between the raw-Cq value of a GOI and a reference gene.

The present invention allows the usage of more than one reference gene: First, the raw-Cq values of the reference genes are averaged, and then the difference between the raw-Cq value of the GOI and the averaged raw-Cq values of the reference genes is calculated. The person skilled in the art knows that first the averages of the replicates for each reference gene and then the average of the reference genes have to be calculated; averaging all replicates of all reference genes in one step would yield a different result due to potential occurrences of "Invalid" replicates.

measurement noise: describes the fact that repeated measurements do not exactly yield exactly the same results. The term measurement noise relates to a random variable describing this effect in a mathematical model as well as its distribution or its standard deviation. The term measurement noise is not restricted to any specific source or cause of such noise; it may be understood as replicate-to-replicate noise with one PCR plate, deviations between specific devices, operators or lots, statistical deviations between devices, operators or lots, or total noise between PCR-based tests.

noise model: mathematical description of the relation between true and measured raw-Cq values. In particular a noise model describes the distribution of raw-Cq values (including their classes "Numeric", "Undetected" and "Invalid") for a fixed (unknown) true raw-Cq value or target amount.

confidence: any information describing the statistically estimated true value of a variable. Variables may be raw-Cq values, delta-Cq values, replicates, averages of replicates, or averages of reference genes. Primarily the term confidence shall be understood as the estimated distribution of the true value of said variable; this is related to the distribution of measured values or estimates for a fixed true value (sec- and interpretation). Confidences may be presented as distributions, approximations to distributions, sets of sampled values, confidence bounds (lower and upper) or standard deviation.

lower bound: Key concept of the present invention. The phrase "lower bound" used in the context of delta-Cq values or their calculation or estimation denotes a fixed number serving as an absolute minimum for delta-Cq values. The rationale for the introduction of a lower bound can be taken from FIG. 3. The lower bound enables estimation of delta-Cq values from raw-Cq values being "Undetected" with finite standard deviation; it thus avoids to reject samples having a poor target concentration in at least one gene. The value of the lower bound may depend on the GOI, the set of reference genes and the application of the delta-Cq values (further processing).

DESCRIPTION OF THE INVENTION

In the following, the invention is described in conjunction with exemplary embodiments, actual examples and figures, which show:

FIG. 1. Calculation process overview.

Figure 2:
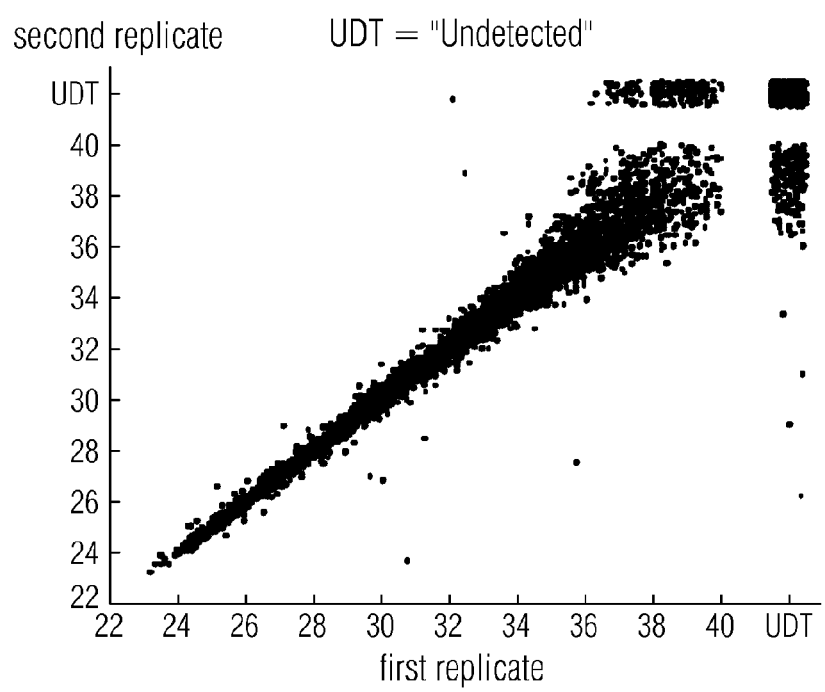

FIG. 2. Scatter plot of raw-Cq value distribution ("Numeric" and "Undetected" types only). Based on such data the skilled person can construct a noise model covering replicate-to-replicate noise.

Figure 3:
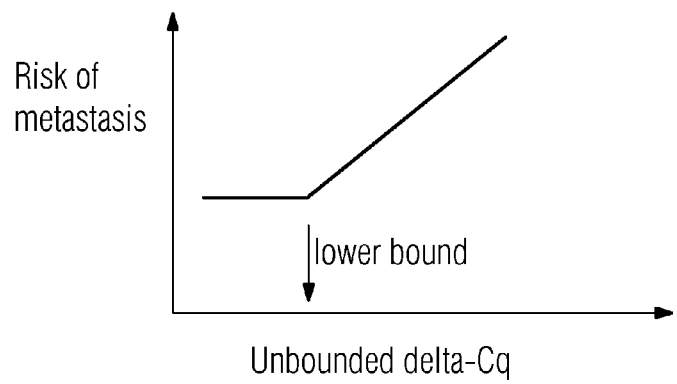

FIG. 3. Effect of a lower bound on the delta-Cq value as illustrated by a qPCR based oncological test. The skilled person knows that delta-Cq values live on a logarithmic scale (logarithm of the number of target molecules) with the consequence of difficult interpretation of small values. Therefore small and very small delta-Cq values should have the same biological impact.

Figure 4:
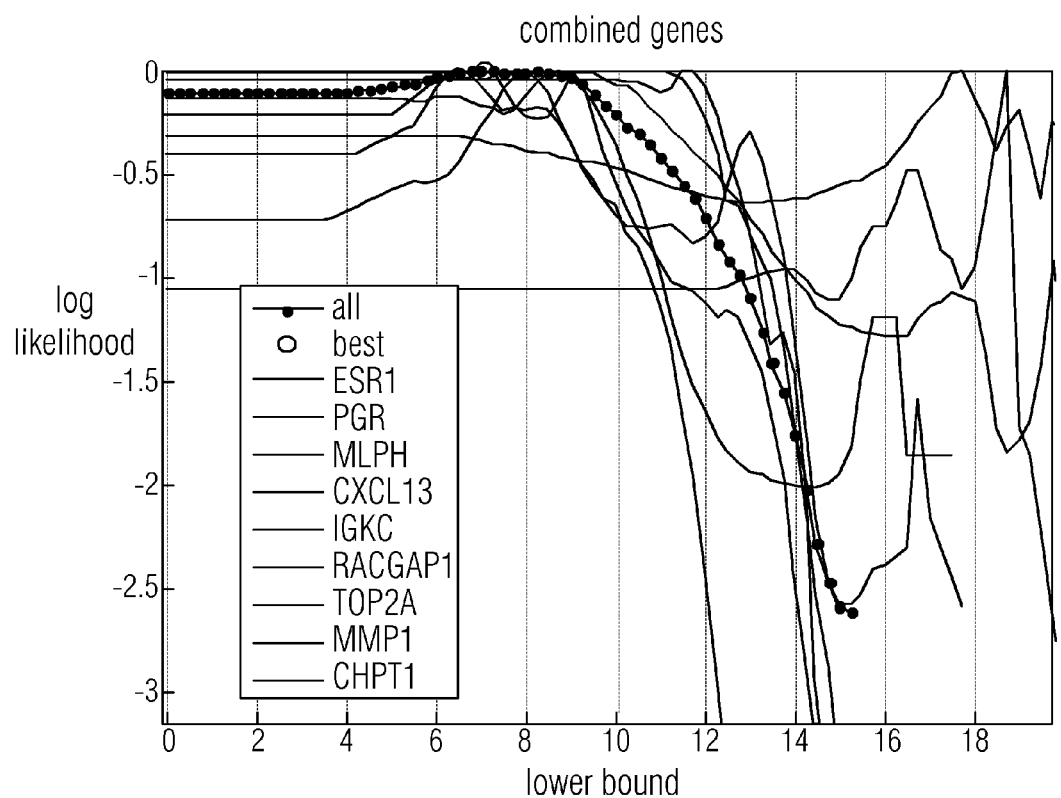

FIG. 4. Determination of lower bound. Based on a training data set for a qPCR based oncological test, the ability of several genes to predict metastasis is examined. Delta-Cq values depend on the choice of the lower bound, thus the lower bound has impact on the association between gene delta-Cq values and metastasis information.

Genes were analyzed separately: The log-likelihood of predicting metastases is drawn as a function of the lower bound. Genes are known to be predictive within this data set and log-likelihood curves were shifted along the y-axis to have zero maximum value for graphical reasons. The "all" curve is the arithmetic mean of the curves of the genes to fit to the same axes.

As one expects the higher the lower bound the more information about metastases is lost. Nevertheless the plot indicates lower bounds less than about 9 not to destroy information significantly. In fact the lower bound was chosen to be 8.5 here.

Figure 5:
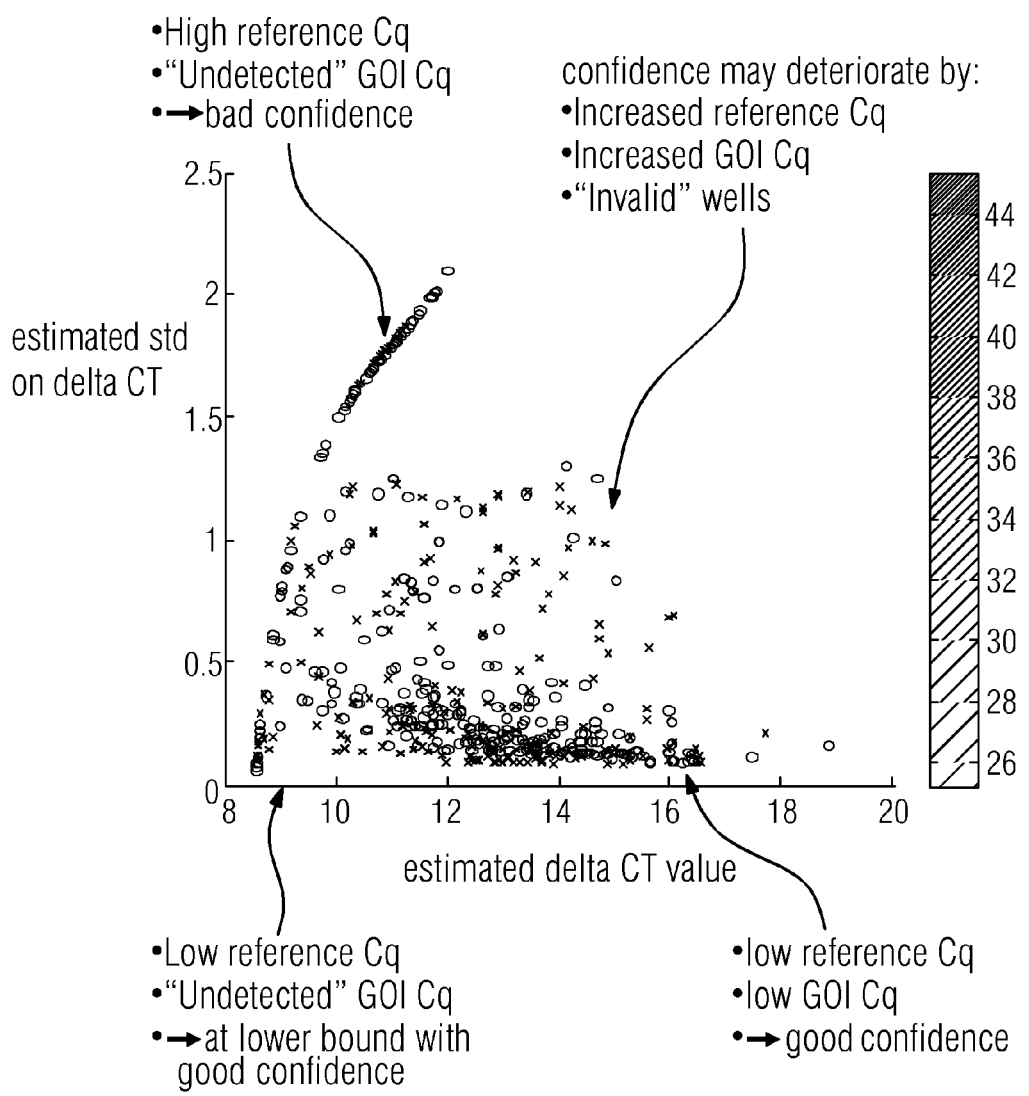

FIG. 5. Scatter plot of estimated delta-Cq values and their estimated confidence (standard deviation). Circles denote real measurements, crosses denote simulated data.

EXAMPLE 1

Illustrative Examples of Delta-Cq Value Calculation (Simplified Overview)

Let c be the raw-Cq value for some GOT and r be the reference gene raw-Cq value (one reference gene only). Then the unbounded delta-Cq value is $$du = 20 - (c - r).$$

Let the lower bound be 8.5, then the (bounded) delta-Cq value is $$d = \max\{du, 8.5\}.$$

For the rationale of bounding see FIG. 3.

The following table shows some examples of measurement results in each row. Columns "data entry" contain raw measurement results, columns "mathematical interpretation" add estimated noise from some noise model to it. The remaining columns are calculated according to the formulas above.

| No | comment | r: reference Cq | | c: GOI raw Cq | | du: delta Cq | d: delta Cq |
| | | data entry | mathematical interpretation | data entry | mathematical interpretation | unbounded, by definition | bounded, by definition |
|---|---|---|---|---|---|---|---|
| A | good RNA yield, high expression | 25 | 25 ± 0.34 | 30 | 30 ± 0.49 | 15 ± 0.60 (g) | 15 ± 0.60 (g) |
| B | bad RNA yield, high expression | 30 | 30 ± 0.49 | 35 | 35 ± 1.16 | 15 ± 1.26 (g) | 15 ± 1.26 (g) |

-continued

|   |   | r: reference Cq | | c: GOI raw Cq | | du: delta Cq | d: delta Cq |
|---|---|---|---|---|---|---|---|
| No | comment | data entry | mathematical interpretation | data entry | mathematical interpretation | unbounded, by definition | bounded, by definition |
| C | good RNA yield, low expression | 25 | 25 ± 0.34 | 38 | 38 ± 1.40 | 7 ± 1.44 (i) | 8.5 (at lower bound) (g) |
| D | intermediate RNA yield, low expression | 28 | 28 ± 0.40 | "Undetermined" | above ≈40 (*) | below ≈8 (p) | 8.5 (at lower bound) (g) |
| E | bad RNA yield, low expression | 30 | 30 ± 0.49 | "Undetermined" | above ≈40 (*) | below ≈10 (p) | between 8.5 and ≈10 (i) |
| F | very bad RNA yield, low expression | 35 | 35 ± 1.16 | "Undetermined" | above ≈40 (*) | below ≈15 (p) | between 8.5 and ≈15 (p) |

Remarks:
(*) The value of 40 also has a confidence interval; this is denoted by the ≈ symbol. For the sake of simplicity and clarity of ideas the ± confidence quantity is omitted here. Nevertheless the present invention considers it.
(g) good confidence
(i) intermediate confidence
(p) poor confidence The PCR machine ran 40 cycles, thus "Undetermined" denotes a raw-Cq value above 40. Sample B is a diluted version of sample A (dilution factor $2^5=32$ if amplification efficiency is perfect), samples D, E and F are diluted versions of sample C (factors $2^3=8$, $2^5=32$ and $2^{10}=1024$).

As one can see bounding has the following effects. Samples A and B are not affected, neither their estimate nor their confidence. Samples C, D and E have improved confidence. Sample F is a hopeless case; no mathematical method can make a confident delta-Cq value estimate as long as the reference raw-Cq value is such large.

EXAMPLE 2

Noise Model A1

For some measured raw-Cq value (gene of interest or reference gene), the standard deviation of the raw-Cq measurement is calculated as std.dev.=log 2($2^{0.3}+2^{((raw-Cq-35)/2)}$).

The model then assumes a normal distribution for the true value with this standard deviation and with expected value equal to the measured raw-Cq value. If "Undetected" was measured the true raw-Cq value distribution is modeled as equal distribution within some interval [a, b], where a is the number of PCR cycles measured and b is derived from the definition of the delta-Cq value using the reference gene values and the lower bound for the delta-Cq value.

EXAMPLE 3

Noise Model A2

Same as noise model A1, but for "Undetected" the true value distribution is blurred at the lower interval bound in order to even give raw-Cq values close below a also a positive probability. The degree of blurring should correspond to the estimated standard deviation for "Numeric" Cq values at a.

EXAMPLE 4

Noise Model A3

Same as noise model A1 or noise model A2, but formula std.dev.=log 2($2^{0.3}+2^{((raw-Cq-35)/2)}$)

describes the standard deviation of the measured raw-Cq values for a fixed true raw-Cq value. This can be converted into a distribution of the true raw-Cq value for a fixed measured raw-Cq value using the Bayesian formula, where an appropriate prior distribution for delta-Cq values must be applied. A possible choice for such a prior distribution could be the (improper) equal distribution over all real numbers.

EXAMPLE 5

Noise Model A4

Same as noise model A3, but with a prior distribution that is derived by sampling from some cohort (i.e. training cohort). Among all samples of the cohort those samples are selected that have reference raw-Cq values below a certain threshold. For them delta-Cq values can be calculated directly by definition with good confidence.

EXAMPLE 6

Noise Model B

It is assumed that the PCR machine runs 40 cycles. Then, for a fixed true raw-Cq value the probability of a measurement to result in "Undetected" is $P(\text{"Undetected"})=\exp(-\exp(-0.657758*(\text{true raw-Cq}-38.5514)))$.

The probability for a "Numeric" observation is $P(\text{"Numeric"})=1-P(\text{"Undetected"})$.

Please note that the true raw-Cq value is unknown and may be larger than the number of cycles run.

If a "Numeric" raw-Cq value was observed, then, for a fixed observed raw-Cq value, the true raw-Cq value is normally distributed with mean equal to the observed raw-Cq value and variance given by the following equation:

variance=$0.0267907+\exp(0.509836*(\text{raw-Cq}-37.3691))$

EXAMPLE 7

Noise Model C

Same as noise models A1-A4 or B, but with extension of further measurement noise sources. While the above noise models only consider replicate-to-replicate noise other sources (device, lot, operator, . . . ) may introduce additional noise. Noise model C considers this by folding raw-Cq and/or delta-Cq distributions with an additional normal distributed noise having zero mean and a standard deviation that estimates further measurement noise sources and that is estimated experimentally.

Overview: Generics of Solutions

Alternative solutions may differ in alternative noise models and alternative mathematical/numerical calculation methods. Calculation methods depend on the chosen noise model and include the following features:

(i) bounds: lower/upper/both (ii) dependence of bounds: GOI, reference genes, application, device used, primer/probe design, SOP used, . . .

(iii) Bayesian prior for raw-Cq values: equal distribution/ equal distribution between bounds/sampling from training cohort/parametric distribution derived from training cohort/ other priors (iv) approximation: normal distribution for all variables/ use samples from training cohort/use equidistant samples/ exact with numeric integration (v) covariance between delta-Cq values of different GOI: ignore/consider

EXAMPLE 8

Outlier Elimination in Replicates

Outlier within replicates may be identified and eliminated as a first processing step. This may be performed for the GOI as well as for each reference gene. Identification of outliers may be realized by application of a noise model to the set of replicates and calculation of a P-value for the null hypothesis "Any real number is the true raw-Cq value" (this P-value is related to the Bayesian evidence). Alternatively, an outher may be identified by estimating a true value with confidence from the other replicates and comparing these to the replicate to test by an appropriate statistic based on some noise model.

Elimination of outliers may be realized by setting them to type "Invalid".

EXAMPLE 9

Outlier Identification in Motives

Outlier identification as described in example 8 can be improved by examining highly correlated genes. These may be different reference genes or different genes from a common motive. By comparing all replicates from all the genes under consideration one may derive P-values of a single replicate or a single gene to be an outlier by methods similar to these described in Example 8: Therefore a noise model as well as a measure of the correlation between genes should be considered.

EXAMPLE 10

Calculation Method for Delta-Cq Values, Overview

In this example we describe a mathematical method to calculate delta-Cq values with confidence as part of a test that predicts a patient's recurrence risk from RNA measurements within a primary breast cancer tissue slide.

The number of molecules of a certain gene in a defined volume of eluate depends on a lot of factors. Among them are the expression of the gene (characterizing tumor properties), the amount of used material (cross sectional area of tumor, slide thickness, number of slides pooled), and the proportions of different cell types (i.e. tumor cells versus fat cells which contain very few RNA compared to their volume).

The first factor is the one we want to extract because we believe it contains the information about the future tumor development. The other factors can not be standardized effectively; but fortunately they affect—more or less—all genes the same way. This enables us to calculate the expression of a gene relatively: We examine the ratio between the numbers of molecules of a gene of interest (GOI) and some so-called reference genes. The reference gene expressions are treated as internal references inherently contained in each sample.

Reference Genes

We distinguish between GOIs on one hand, whose relative expression predicts the risk of recurrence, and reference genes on the other hand which are used to refer to. Not every gene is suitable for reference. Reference genes should be known to have a constant expression level and should be able to be measured precisely. High expressed genes can be measured more precisely than low expressed ones, thus reference genes are chosen among the high expressers. Biologically, probably no gene has an exactly constant expression level. Nevertheless there are some genes that have very similar expression levels between patients (housekeepers) and are thus suitable for usage as reference genes.

Since there is no perfect reference gene and because we need to have a robust reference this example assumes two reference genes to be measured and the average of their raw-Cq values to be used for delta-Cq value calculation. Throughout this text we use two reference genes; nevertheless a generalization to more reference genes is straight forward and can easily be derived by a person skilled in the art. Our software implementation is able to handle arbitrary numbers of reference genes.

Examples of reference genes are RPL37A, GAPDH, CALM2, PPIA, and OAZ1.

Delta-Cq Values

Delta-Cq values in this example can be written as $$d = 20 - \left(g - \frac{1}{2}(r^{(1)} + r^{(2)})\right), \quad (1)$$

where d is the delta-Cq value, g is the raw-Cq value for some GOI and $r^{(1)}$ and $r^{(2)}$ are the raw-Cq values of our two reference genes. Since Cq values are logarithms of molecule numbers the ratios of molecules mentioned above transform into differences of Cq values, i.e. the difference inside the outer brackets.

The part outside the outer brackets on the right side of equation (1) seems to be arbitrary at first glance. We chose this definition for two reasons: We want higher delta-Cq values to correspond to higher expressions (this explains the minus sign in front of the brackets) and we did not want to deal with negative numbers (this explains the constant 20).

Raw-Cq Values

Raw-Cq values is this example are measured in triplicates and we describe our approach in this text using three replicates: Less than three replicates makes outlier elimination impractical. The generalization to more or less than three replicates is straight forward and may easily derived by a person skilled in the art.

Triplicates are three independent measurements for each sample slide and each gene, however on the same plate. Each replicate can have one of three types of result:

"Numeric": Most replicates result in a real number denoting the quantification cycle which is an (interpolated) cycle number. This just follows the usual definition of raw-Cq values.

"Undetected": In some cases the fluorescence curve did never show a signal above background noise during all cycles. In this example we run 40 cycles, thus "Undetected" means that the amount of RNA in the eluate is as small as or smaller than the amount of RNA that would result in a raw-Cq value of 40.

It is important to note that "Undetected" is a valid and informative result of the measurement. It just means that the gene is low expressed. FIG. 2 demonstrates that "Undetected" nearly always occurs with "Numeric" values close to 40 or other "Undetected" values within triplicates in our data.

"Invalid": In some rare cases the fluorescence curve was invalid for different reasons. In this example we practice quality control by manual inspection: Each curve is examined by a technician and those curves with abnormal behavior are flagged "Invalid". As an alternative it is also possible to replace this manual inspection by an automatic and reproducible procedure.

"Invalid" values denote failure in measurement and are ignored. As long as not all values of a triplicate are "Invalid" a value can be estimated. Our model assumes "Invalid" values to occur non-informatively.

In summary, examples of raw-Cq values are 23.5, 37.9, "Undetected", and "Invalid". In this example outliers are detected and converted to "Invalid" prior to the calculations described here.

Interpretation of "Undetected"

In this example we use delta-Cq values to predict a patient's recurrence risk. Thus for each gene we need a numeric value to put into our risk score formula. Unfortunately "Undetected" gives us incomplete information. Let us discuss this in some example samples:

| Sample No. | raw-Cq of GOI: g | raw-Cq of references: $r^{(1)}, r^{(2)}$ | delta-Cq according to equation (1) |
|---|---|---|---|
| A | 32 | 20 | 8 |
| B | 37 | 25 | 8 |
| C | "Undetected" (i.e. "≥40") | 30 | ≤10 |
| D | "Undetected" (i.e. "≥40") | 35 | ≤15 |

Sample A describes a typical sample with high yield (raw-Cq of reference genes is small) and low expressed gene (raw-Cq of GOI is much greater than reference genes). From the raw-Cq values of the GOI and the references (both are assumed to have the same value) we can calculate the delta-Cq value from equation (1). Now we dilute sample A by a factor of $2^5=32$ and call it sample B: Compared to sample A both raw-Cq values raise by 5 Cq values, but the delta-Cq value remains unchanged. This is an important feature because sample dilution obviously does not change the recurrence risk of the patient. Samples C and D are again sequential dilutions by a factor 32 each. The raw-Cq value of the reference genes raise up in steps of 5 Cq values, but the GOI does not give a signal any more. Thus, we cannot assign a "Numeric" value to the raw-Cq value, but since we know that 40 cycles were ran we can say that the theoretical raw-Cq value of the GOI must be 40 or above. In other words "Undetected" is interpreted as the interval [40,∞[. We can substitute this into equation (1), which gives us a delta-Cq value which again is an interval. Unfortunately the delta-Cq interval depends on the reference raw-Cq value. The interpretation is very natural:

For high yield (samples A and B) we can estimate the delta-Cq value exactly.

For intermediate yield (sample C) we cannot determine the delta-Cq value exactly, but we can distinguish between low expression (e.g. delta-Cq below 10), intermediate expression (e.g. delta-Cq between 10 and 13), and high expression (e.g. delta-Cq above 13). This means that although the delta-Cq value is not known exactly we might still assign informative and valuable recurrence risk classes.

For bad yield (sample D) we can not distinguish between low and high expression. This means that we have to discard this sample.

"Undetected" and Risk Scores

As discussed above the delta-Cq value may either be a real value or an interval of form $]-\infty, d_{max}]$. This is still not suitable for recurrence risk prediction. We demonstrate this by an example. Two of the most important motives for recurrence prediction are proliferation (higher proliferation means higher risk) and immune system (higher immune system activity means lower risk). A simple recurrence risk score might look like $$s=0.6d_1-0.4d_2, \quad (2)$$

where $d_1$ denotes the delta-Cq value of some proliferation gene and $d_2$ one of an immune gene. Setting the delta-Cq values to intervals of forms as discussed above has different effects on the score form since the coefficients of the genes in equation (2) have different signs. Going back to raw-Cq values we find the form of the score s to depend on the raw-Cq value types of the GOIs:

| | | proliferation gene | |
|---|---|---|---|
| form of score s | | "Numeric" | "Undetected" |
| immune gene | "Numeric" | exact $s \in \Re$ | $]-\infty, s_{max}]$ |
| | "Undetected" | $[s_{min}, \infty[$ | $]-\infty, \infty[$ |

The Lower Bound

To report these very different forms of scores makes not much sense, because they cannot be compared to each other; the clinician or patient needs to know whether the risk is low or high.

Fortunately this interval form information is not the end of the rope. For each gene we know the typical range of delta-Cq values and the associated risks. In particular we may not need to distinguish between low expression (e.g. delta-Cq between 8 and 10) and very low expression (e.g. delta-Cq<8) if there is no difference in the recurrence rate between the two patient groups. If so, we could assign the same risk score to samples having delta-Cq values 5, 8, 10, ≤8, or ≤10. The numerical realization of this grouping mechanism is to define a lower bound L on delta-Cq values. One possible way to account for the lower bound is to modify definition (1) to $$d = \max\left\{20 - \left(g - \frac{1}{2}(r^{(1)} + r^{(2)})\right), L\right\}. \quad (3)$$

This definition of delta-Cq values prohibits infinite intervals and so reduces the uncertainty of delta-Cq values to a bounded interval. Let us look on some example samples again (samples A-D are from the table above) using the lower bound L=10:

| Sample No. | raw-Cq of GOI: g | raw-Cq of references: $r^{(1)}, r^{(2)}$ | delta-Cq according to equation (3) |
|---|---|---|---|
| A | 32 | 20 | 10 |
| B | 37 | 25 | 10 |
| C | "Undetected" (i.e. "≥40") | 30 | 10 |
| D | "Undetected" (i.e. "≥40") | 35 | [10, 15] |
| E | 36 | 30 | 14 |
| F | "Undetected" (i.e. "≥40") | 35 | [14, 15] |

For samples A-C the delta-Cq value is at the lower bound. Please note that even in case C with an "Undetected" raw-Cq value there is no longer uncertainty in the delta-Cq value. Only sample D with very bad yield shows a large uncertainty in the delta-Cq value estimation. Samples E and F show a different case with high expression in two dilution steps. Even for bad yield the delta-Cq value can be estimated within a +/−0.5 Cq value confidence interval. This might be precise enough to distinguish between high and low recurrence risk. When thinking about quality control the two example samples demonstrate that looking at the yield (i.e. raw-Cq value of reference genes) only one cannot give a good criterion which samples to predict and which to refuse.

The determination of the lower bound is discussed here only briefly. The introduction of a lower bound in general becomes necessary by the observation that "Undetected" raw-Cq values lead to infinite interval estimations in delta-Cq values. What arguments are used to determine the concrete value of L? First, the higher L the more information is lost; in particular this affects genes and samples having "Numeric" values. Since we are interested in information about the recurrence risk this kind of information loss can only be assessed using patient's outcome information (examining non-linearity between delta-Cq and outcome). Second, the lower L the higher the uncertainty in delta-Cq values; this is true for the confidence interval width as well as for the signal-to-noise ratio. Please note, that L must be independent of patients. We addressed these topics in a detailed discussion and found a value for L indicating a compromise. Since the statistical robustness of such a compromise is not very high we chose the same lower bound for all genes.

EXAMPLE 11

Calculation Method for Delta-Cq Values, Bayesian Estimation

This example describes the estimation of delta-Cq values and their confidence intervals in mathematical detail. We use a Bayesian methods approach to calculate delta-Cq value distributions.

To estimate a delta-Cq value we need three parts:

Estimation of the true raw-Cq values of the reference genes: $r^{(1)}, r^{(2)}$. We assume two reference genes here; the skilled person can easily generalize to a higher or smaller number of reference genes.

Consideration of the lower bound: $d \geq L$.

Estimation of the true raw-Cq values of GOI (gene of interest): g.

In a processing view we perform calculations in this order and also discuss them here in this order.

General Notations

We denote unknown true values by $r^{(j)}$, g (raw-Cq values), and d (delta-Cq value). We assume measurements in triplicates and denote the measurement values by $r_i^{(j)}$ and $g_i$, respectively, where i=1, . . . , 3 runs over replicates. The skilled person can easily generalize to a higher or smaller number of replicates. Let D ("data") denote all measured values for a particular sample and fixed GOI, thus we have $D=\{g_1, \ldots, g_3, r_1^{(1)}, \ldots, r_3^{(1)}, r_1^{(2)}, \ldots, r_3^{(2)}\}$.

When examining the covariance of two genes we denote the true values as $g^{(1)}, g^{(2)}, d^{(1)}$, and $d^{(2)}$, denote measurements by $g_i^{(j)}$ for $j \in \{1,2\}$, and set $D=\{g_1^{(1)}, \ldots, g_3^{(1)}, g_1^{(2)}, \ldots, g_3^{(2)}, r_1^{(1)}, \ldots, r_3^{(1)}, r_1^{(2)}, \ldots, r_3^{(2)}\}$, respectively. Also see the section at the end of this example for a complete list of symbols.

Estimation of Reference Genes

To estimate the true value of a reference gene means to calculate the posterior probability of its true value given the measurement results. This can be done using the Bayesian formula.

$$p(r^{(j)} | D) = \frac{p(D | r^{(j)})p(r^{(j)})}{p(D)} \quad (4)$$

The three probabilities on the right hand side can be discussed separately. The prior distribution of the true value is chosen to be equal for all values, $$p(r^{(j)}) = \text{const.} \quad (5)$$

With "const" we abbreviate factors in equations that are independent of all of the true values g, r, and d. They depend on the data D and may differ between transformation steps. The choice of an equal prior makes is completely non-informative, because each $r^{(j)} \in \mathfrak{R}$ has the same probability and no estimation bias is introduced (see below). The prior is not normalizable, i.e. $\int p(r^{(j)}) dr^{(j)} \neq 1$ for all constants, and thus the prior is called an improper prior. The Bayes equation (4) can be written as $$p(r^{(j)} | D) = \frac{p(D | r^{(j)})p(r^{(j)})}{\int p(D | r^{(j)})p(r^{(j)}) dr^{(j)}}, \quad (6)$$

and one can now see that the same constant appears in the numerator as well as the denominator. Most non-informative priors are improper and their usage is common practice. The denominator in equation (4) is—as seen—only a normalizing factor. Since it does not depend on the true value we abbreviate it as some constant and rewrite equation (4).

$$p(r^{(j)} | D) = \text{const} \cdot p(D | r^{(j)}) \quad (7)$$

Obviously only the likelihood factor is left to determine the reference gene true value distribution. Only measurements of reference gene j are affected by the true value, $$p(r^{(j)}|D) = \text{const} \cdot p(r_1^{(j)}, \ldots, r_1^{(j)}|r^{(j)}), \qquad (8)$$

and these measurements are assumed to be independent.

$$p(r^{(j)}|D) = \text{const} \cdot \prod_i p(r_i^{(j)}|r^{(j)}) \qquad (9)$$

Since the noise model in this example estimates the distribution of the true value for a fixed measured value (not the other way around), we have to apply the Bayes formula again to each factor on the right hand side.

$$p(r^{(j)}|D) = \text{const} \cdot \prod_i \frac{p(r^{(j)}|r_i^{(j)}) p(r_i^{(j)})}{p(r^{(j)})} \qquad (10)$$

The denominator is already defined by equation (5), and the prior distribution of the measurement is a constant because it does not depend on the true value. Thus the equation simplifies to $$p(r^{(j)}|D) = \text{const} \cdot \prod_i p(r^{(j)}|r_i^{(j)}). \qquad (11)$$

Now we can apply the noise model. If we observe an "Undetected" value for one of the replicates (which was not removed by outlier elimination procedure) we reject the sample. This is because raw-Cq values of reference genes are typically lower than those for GOIs, and if the reference is "Undetected" most GOIs will also be "Undetected" and we will not be able to estimate delta-Cq values properly. If any of the replicates is "Invalid" or an outlier, we just omit the corresponding factor. Thus, for the remaining "Numeric" replicates we apply the noise model, which here consists of the noise function $\sigma(.)$:

$$p(r^{(j)}|D) = \text{const} \cdot \prod_i \frac{1}{\sqrt{2\pi}\, \sigma(r_i^{(j)})} \exp\left(-\frac{(r^{(j)} - r_i^{(j)})^2}{2\sigma(r_i^{(j)})^2}\right). \qquad (12)$$

Some transformation steps $$p(r^{(j)}|D) = \text{const} \cdot \prod_i \exp\left(-\frac{(r^{(j)} - r_i^{(j)})^2}{2\sigma(r_i^{(j)})^2}\right)$$

$$= \exp\left(-\frac{1}{2} \sum_i \frac{(r^{(j)} - r_i^{(j)})^2}{\sigma(r_i^{(j)})^2} + \text{const}\right)$$

$$= \exp\left(-\frac{1}{2}\left((r^{(j)})^2 \sum_i \frac{1}{\sigma(r_i^{(j)})^2} - 2r^{(j)} \sum_i \frac{r_i^{(j)}}{\sigma(r_i^{(j)})^2} + \text{const}\right)\right)$$

$$= \exp\left(-\frac{1}{2}\left(\sum_i \frac{1}{\sigma(r_i^{(j)})^2}\left(r^{(j)} - \left(\sum_i \frac{1}{\sigma(r_i^{(j)})^2}\right)^{-1} \sum_i \frac{r_i^{(j)}}{\sigma(r_i^{(j)})^2}\right)^2 + \text{const}\right)\right)$$

show that the data-conditional true value is normally distributed with parameters $$\mu_r^{(j)} := E[r^{(j)}|D] = \left(\sum_i \frac{1}{\sigma(r_i^{(j)})^2}\right)^{-1} \sum_i \frac{r_i^{(j)}}{\sigma(r_i^{(j)})^2} \qquad (13)$$

$$(\sigma_r^{(j)})^2 := \text{VAR}[r^{(j)}|D] = \sum_i \frac{1}{\sigma(r_i^{(j)})^2}$$

Our implementation calculates these values this way. Obviously the estimated mean is a weighted average of the measured values where the weighting factors are $\sigma(r_i^{(j)})^{-2}$: The higher the measurement noise the lower the weighting factor. Nevertheless, for most samples the raw-Cq value of the references will be below 30, where the noise is nearly constant. Under this approximation the estimated mean simply is the arithmetic average of replicates.

Our delta-Cq value definition uses the average of two reference genes. Before we proceed with the GOIs we summarize our reference genes into one variable. We define $$r = \frac{1}{2}(r^{(1)} + r^{(2)}). \qquad (14)$$

Since the replicates of the different reference genes are independent, variables $r^{(1)}$ and $r^{(2)}$ are independent, too. Using random variable calculus rules we find that r is normally distributed with parameters $$\mu_r := E[r|D] = \frac{1}{2}(\mu_r^{(1)} + \mu_r^{(2)}) \qquad (15)$$

$$\sigma_r^2 := \text{VAR}[r|D] = \frac{1}{4}((\sigma_r^{(1)})^2 + (\sigma_r^{(2)})^2)$$

Our implementation again calculates these values.

Estimation of Gene of Interest

As will be seen below the posterior distribution of the true raw-Cq value of the GOI depends on the reference gene. The main reason for this is the lower bound constraint on the delta-Cq values. Nevertheless, the likelihood (i.e. the probability of observed measurement values) does not depend on the reference gene. This section derives the likelihood of raw-Cq values of a GOI from the noise model.

We measure three replicates and assume they are independent.

$$p(g_1, \ldots, g_3|g) = \prod_i p(g_i|g) \qquad (16)$$

Remember that a GOI measurement results in one of three result types: "Numeric" (a real number denoting a cycle), "Undetected" (no signal within all cycles run), or "Invalid" (some failure for this replicate). "Invalid" replicates are assumed to give no information about the true value and we simply omit the corresponding factors on the right hand side of equation (16). Function $\upsilon(.)$ is part of the noise model and estimates the probability of "Undetected" for a given true raw-Cq value.

$$p(g_i|g) = \begin{cases} \upsilon(g), & g_i \text{ is "Undetected"} \\ (1-\upsilon(g)) \cdot p(g_i|g, g_i \text{ is "Numeric"}), & g_i \text{ is "Numeric"} \end{cases} \quad (17)$$

While "Undetected" determines the likelihood for a single replicate completely by function $\upsilon(.)$, we have to consider the measurement noise in addition for "Numeric" values. Like with the reference values the noise model describes the distribution of the true value for a fixed measured values; thus we first have to apply Bayes formula.

$$p(g_i|g, g_i \text{ is "Numeric"}) = \frac{p(g|g_i, g_i \text{ is "Numeric"})p(g_i|g_i \text{ is "Numeric"})}{p(g|g_i \text{ is "Numeric"})} \quad (18)$$

Again, we reduce the normalizing denominator to a constant and choose the data prior in the numerator as constant.

$$p(g_i|g, g_i \text{ is "Numeric"}) = \text{const} \cdot p(g|g_i, g_i \text{ is "Numeric"}) \quad (19)$$

The likelihood is taken from the noise model as a normal distribution:

$$p(g|g_i, g_i \text{ is "Numeric"}) = \frac{1}{\sqrt{2\pi}\,\sigma(g_i)} \exp\left(-\frac{(g-g_i)^2}{2\sigma^2(g_i)}\right) \quad (20)$$

We can summarize equations (16) to (20) to a function of the form $$p(g_1, \ldots, g_3|g) = \text{const} \cdot \upsilon^m(g)(1-\upsilon(g))^n \exp\left(-\frac{(g-\mu_g)^2}{2\sigma_g^2}\right) \quad (21)$$

with appropriate constants $m, n, \mu_g$, and $\sigma_g$. In case there are no "Numeric" measurements we define $\mu_g=0$ and $\sigma_g=\infty$. Our implementation calculates these constants and we define a help function $$h(g) := \upsilon^m(g)(1-\upsilon(g))^n \exp\left(-\frac{(g-\mu_g)^2}{2\sigma_g^2}\right). \quad (22)$$

Later we evaluate the likelihood of all replicates of the GOI by calculating help function values point-wise numerically.

Delta-Cq Value Distribution

The delta-Cq value definition in equation (1) and the summary reference value definition in equation (14) lead to the simplified delta-Cq value definition $$d = 20 - g + r, \quad (23)$$

which will be used below. Please keep in mind that $g|D$ and $r|D$ are not independent because of the lower bound constraint on the delta-Cq value. In the following we calculate the posterior delta-Cq value distribution by examining the bivariate $p(g,r|D)$ distribution.

The reference value can be estimated independently from GOIs, thus we give a separate factor to it, which already was determined above.

$$p(g,r|D) = p(g|D,r)p(r|D) \quad (24)$$

We now analyze the reference-conditional distribution. First, the GOI distribution only depends on the GOI measurements when the reference value is fixed.

$$p(g|D,r) = p(g|g_1, \ldots, g_3, r) \quad (25)$$

Now we apply Bayes formula.

$$p(g|D, r) = \frac{p(g_1, \ldots, g_3|g, r)p(g|r)}{p(g_1, \ldots, g_3|r)} \quad (26)$$

We discuss the three probabilities on the right hand side separately. The denominator is only a normalizing factor for the left hand probability and thus can be set to some constant.

$$p(g_1, \ldots, g_3|r) = \text{const} \quad (27)$$

The prior probability $p(g|r)$ is chosen non-informatively, but reflects the lower bound constraint $d \geq L$, which was already discussed above. Thus we set $$p(g|r) = \begin{cases} 1, & 20-g+r \geq L \\ 0, & \text{else} \end{cases} = H(20-g+r-L), \quad (28)$$

where $H(.)$ is the Heaviside step function. This again is an improper prior. The remaining probability in equation (26) is the likelihood. Since the GOI measurements only depend on its true value if known we can rearrange the likelihood to $$p(g_1, \ldots, g_3|g, r) = p(g_1, \ldots, g_3|g) \quad (29)$$

Combining equations (26) to (29) we get $$p(g|D,r) = \text{const} \cdot p(g_1, \ldots, g_3|g)H(20-g+r-L). \quad (30)$$

We now combine equations (24) and (30), replace the likelihood of the GOI measurements by our help function (22), and replace the posterior reference distribution by our results from above, (12) to (15).

$$p(g, r|D) = c \cdot h(g)H(20-g+r-L)\frac{1}{\sqrt{2\pi}\,\sigma_r}\exp\left(-\frac{(r-\mu_r)^2}{2\sigma_r^2}\right) \quad (31)$$

Here we assigned the constant factor the name c because it will play an important role later. Please note that c depends on constants $m, n, \mu_g, \sigma_g$ (as function $h(.)$ does), $L$, $\mu_r$ and $\sigma_r$, but not on g nor r.

Estimation of delta-Cq values has now been partially separated rated into factors: factor $h(g)$ does not depend on the reference while the last factor does not depend on the GOI true value. Only the Heaviside factor connects them, it just determines an integration limit.

Delta-Cq Value Calculation for normal distributions

In this and the next section we use equation (31) to calculate several features of random variable d. The reason for this is just to speed up processing time of our implementation. The special case we consider first occurs quite often and can be solved analytically; it is:

There is no "Undetected" GOI replicate and g|D and r|D are approximately independent.

These conditions need further discussion. The first condition targets factor h(g) in equation (31), the second aims on the Heaviside factor. Remember that function h(.) as defined by equation (22) is determined through constants $m, n, \mu_g$, and $\sigma_g$. If there is no "Undetected" GOI replicate then $m=n=0$ and h(g) describes a normal distribution with mean and variance $\sigma_g^2$. We look at the second condition only if the first is fulfilled. In this case we have $$g|D \propto N(\mu_g, \sigma_g^2) \text{ and } r|D \propto N(\mu_r, \sigma_r^2), \tag{32}$$

and the corresponding delta-Cq distribution (neglecting the Heaviside factor) would be $$d|D \propto N(20-\mu_g+\mu_r, \sigma_g^2+\sigma_r^2). \tag{33}$$

Random variables g|D and r|D are approximately independent if the corresponding delta-Cq value is far away from the lower bound with high probability. We state condition 2 more precisely as $$20-\mu_g+\mu_r-L \geq 4(\sigma_g^2+\sigma_r^2). \tag{34}$$

With this condition the probability of the Heaviside factor in equation (31) being zero is $<3.2 \cdot 10^{-5}$. Our approximation is defined as to set it never zero and with this equation (31) simplifies to $$p(g, r|D) = c \cdot \exp\left(-\frac{(r-\mu_g)^2}{2\sigma_g^2}\right) \cdot \exp\left(-\frac{(r-\mu_r)^2}{2\sigma_r^2}\right). \tag{35}$$

Obviously g|D and r|D become independent. With this, the delta-Cq value distribution is determined by (33) including all of its univariate features.

In addition to this we need to calculate the covariance between two GOIs. For this task we require both conditions to be fulfilled for both GOIs, otherwise we proceed as described in the next section. If all conditions are fulfilled we have $$d^{(1)}=20-g^{(1)}+r \text{ and } d^{(2)}=20-g^{(2)}+r \tag{36}$$

with (approximately) independent raw-Cq values. Please note that in the general case $g^{(1)}|D$ and $g^{(2)}|D$ depend on each other only via the reference, because their replicates are independent measurements (see below for a more detailed discussion). We now calculate the covariance straight forward.

$$\begin{aligned}
\text{COV}[d^{(1)}, d^{(2)}|D] &= E[(d^{(1)} - E[d^{(1)}|D]) \cdot (d^{(2)} - E[d^{(2)}|D])|D] \quad (37)\\
&= E[\underbrace{(-g^{(1)} + \mu_g^{(1)}}_{\text{zero mean}} + r - \mu_r) \cdot \\
&\quad \underbrace{(-g^{(2)} + \mu_g^{(2)} + r - \mu_r)}_{\text{independent of } g_1}|D] \\
&= E[\underbrace{(r - \mu_r)}_{\text{independent of } g_2} \cdot \\
&\quad \underbrace{(-g^{(2)} + \mu_g^{(2)}}_{\text{zero mean}} + r - \mu_r)|D] \\
&= E[(r-\mu_r) \cdot (r-\mu_r)|D] \\
&= \text{VAR}[r|D] \\
&= \sigma_r^2
\end{aligned}$$

General Delta-Cq Value Calculation

In this section we use equation (31) in the general case to calculate features of random variable d. Therefore we use the bivariate distribution of g and r and calculate the expected value and the variance from it. We start with the definitions of the expected value and the variance.

$$E[d|D] = \int\int (20 - g + r) \cdot p(g, r|D) dg dr \tag{38}$$

$$\begin{aligned}
\text{VAR}[d|D] &= E[(d - E[d|D])^2|D] \\
&= E[d^2|D] - 2E[d|D]E[d|D] + E[d|D]^2 \\
&= E[d^2|D] - E[d|D]^2
\end{aligned}$$

$$E[d^2|D] = \int\int (20 - g + r)^2 \cdot p(g, r|D) dg dr$$

Since we do not know constant c in equation (31) we have to calculate an additional integral to determine it.

$$1 = \iint p(g, r|D) dg dr \tag{39}$$

Abbreviating the true reference value distribution function by $$f(r) := \frac{1}{\sqrt{2\pi}\,\sigma_r} \exp\left(-\frac{(r-\mu_r)^2}{2\sigma_r^2}\right) \tag{40}$$

we substitute the joint probabilities of the above integrals by the right hand side of equation (31).

$$1 = \iint c \cdot h(g) H(20-g+r-L) f(r) dg dr$$

$$E[d|D] = \iint (20-g+r) \cdot c \cdot h(g) H(20-g+r-L) f(r) dg dr$$

$$E[d^2|D] = \iint (20-g+r)^2 \cdot c \cdot h(g) H(20-g+r-L) f(r) dg dr$$

We then concentrate the reference-dependents factors into the inner integral and move all other factors out of it.

$$\begin{aligned}
1 &= c \cdot \int h(g) \cdot \int H(20-g+r-L) f(r) dr dg \quad (42)\\
&= c \cdot \int h(g) \cdot \int_{g+L-20}^{\infty} f(r) dr dg
\end{aligned}$$

$$\begin{aligned}
E[d|D] &= c \cdot \int h(g) \cdot \int (20-g+r) \cdot H(20-g+r-L) \quad (43)\\
&\quad f(r) dr dg \\
&= c \cdot \int h(g) \cdot \int_{g+L-20}^{\infty} (20-g+r) \cdot \\
&\quad f(r) dr dg
\end{aligned}$$

$$\begin{aligned}
E[d^2|D] &= c \cdot \int h(g) \cdot \int ((20-g)^2 + 2(20-g)r + r^2) \cdot \quad (44)\\
&\quad H(20-g+r-L) f(r) dr dg \\
&= c \cdot \int h(g) \cdot \int_{g+L-20}^{\infty} ((20-g)^2 2(20-g)r + r^2) \cdot \\
&\quad f(r) dr dg
\end{aligned}$$

With respect to r the inner integrals consist of a polynomial of grade 2 at most multiplied with the normal distribution probability density. If we allow the well-known error function $$\text{Erf}(x) := \frac{2}{\sqrt{\pi}} \int_0^x \exp(-t^2) dt \quad (45)$$

to be called elementary we can calculate these integrals analytically. We start with the monomials.

$$\int_{g+L-20}^{\infty} f(r) dr = \frac{1}{2}\left(\text{Erf}\left(\frac{\mu_r - g - L + 20}{\sqrt{2}\,\sigma_r}\right) + 1\right) \quad (46)$$

$$\int_{g+L-20}^{\infty} rf(r) dr = \frac{\sigma_r}{\sqrt{2\pi}} \exp\left(-\frac{(\mu_r - g - L + 20)^2}{2\sigma_r^2}\right) +$$
$$\frac{\mu_r}{2}\left(\text{Erf}\left(\frac{\mu_r - g - L + 20}{\sqrt{2}\,\sigma_r}\right) + 1\right)$$

$$\int_{g+L-20}^{\infty} r^2 f(r) dr = \frac{\sigma_r(\mu_r + g + L - 20)}{\sqrt{2\pi}} \exp$$
$$\left(-\frac{(\mu_r - g - L + 20)^2}{2\sigma_r^2}\right) +$$
$$\frac{\mu_r^2 + \sigma_r^2}{2}\left(\text{Erf}\left(\frac{\mu_r - g - L + 20}{\sqrt{2}\,\sigma_r}\right) + 1\right)$$

To have a more compact form we introduce some abbreviating constants.

$$\alpha(g) := \frac{1}{2}\left(\text{Erf}\left(\frac{\mu_r - g - L + 20}{\sqrt{2}\,\sigma_r}\right) + 1\right) \quad (47)$$

$$\beta(g) := \frac{\sigma_r}{\sqrt{2\pi}} \exp\left(-\frac{(\mu_r - g - L + 20)^2}{2\sigma_r^2}\right)$$

With them the monomials simplify a lot.

$$\int_{g+L-20}^{\infty} f(r) dr = \alpha(g) \quad (48)$$

$$\int_{g+L-20}^{\infty} rf(r) dr = \beta(g) + \mu_r \alpha(g)$$

$$\int_{g+L-20}^{\infty} r^2 f(r) dr = (\mu_r + g + L - 20)\beta(g) + (\mu_r^2 + \sigma_r^2)\alpha(g) \quad (45)$$

We substitute the inner integrals in equations (42) to (44) by this.

$$1 = c \cdot \int h(g) \cdot \alpha(g) dg \quad (49)$$

$$E[d|D] = c \cdot \int h(g) \cdot ((20 - g + \mu_r)\alpha(g) + \beta(g)) dg \quad (50)$$

$$E[d^2|D] = c \cdot \int h(g) \cdot (((20 - g + \mu_r)^2 + \sigma_r^2)\alpha(g) + (20 - g + L + \mu_r)\beta(g)) dg \quad (51)$$

Constant c can now be calculated by numerical integration over g using equation (49). The expected value can then be determined by numerical integration using the equation (50) and the variance via (51). Please note that no transformation or substitution of integration variable g has been done and all three integrals have the same limits, thus the implementation can speed up by integrating them "in parallel" (Matlab function quadv), i.e. running one integration on a three-dimensional integrand. Since the integrands represent random variable distributions numerical integration can be interpreted as drawing (special) samples from the distribution and calculating features from the finite set of samples. In this context parallel integration simply means that for all features the same samples are used.

Delta-Cq Covariance Calculation

Now we calculate the covariance between two GOIs. Therefore we first specify the joint raw-Cq value distribution and then extend equation (31) to two GOIs appropriately. The joint distribution of all three raw-Cq values can be written as $$p(g^{(1)}, g^{(2)}, r|D) = p(g^{(1)}, g^{(2)}|D, r) p(r|D). \quad (52)$$

As stated above the raw-Cq value distribution of a GOI depends on the reference value through the lower bound constraint, but the reference value distribution itself is independent. We now assume in addition, that the raw-Cq values of the GOIs are independent for a fixed reference value.

$$p(g^{(1)}, g^{(2)}, r|D) = p(g^{(1)}|D, r) p(g^{(2)}|D, r) p(r|D) \quad (53)$$

We apply some basic transformations to end up in a form using the right hand side of equation (31). Please note that the true reference value is normally distributed and thus has a positive probability density for every value.

$$p(g^{(1)}, g^{(2)}, r|D) = \frac{p(g^{(1)}, r|D)}{p(r|D)} \frac{p(g^{(2)}, r|D)}{p(r|D)} p(r|D) \quad (54)$$
$$= \frac{p(g^{(1)}, r|D) p(g^{(2)}, r|D)}{p(r|D)}$$

We can now substitute the numerator using equation (31) and denominator using the results from above to derive a concrete form for the joint raw-Cq value distribution.

$$p(g^{(1)}, g^{(2)}, r|D) = c^{(1)} c^{(2)} h(g^{(1)}) h(g^{(2)}) H(20 - g^{(1)} + r - L) \cdot \quad (55)$$
$$H(20 - g^{(2)} + r - L) \frac{1}{\sqrt{2\pi}\,\sigma_r} \exp$$
$$\left(-\frac{(r - \mu_r)^2}{2\sigma_r^2}\right)$$
$$= c^{(1)} c^{(2)} h(g^{(1)}) h(g^{(2)}) H(20 - \max\{g^{(1)}, g^{(2)}\} +$$
$$r - L) \cdot \frac{1}{\sqrt{2\pi}\,\sigma_r} \exp\left(-\frac{(r - \mu_r)^2}{2\sigma_r^2}\right)$$

Please note that by construction any feature of a GOIs delta-Cq value distribution is consistent to what was calculated in the previous section: $E[d^{(1)}|D]$ and $VAR[d^{(1)}|D]$ do not depend on whether they are calculated from $p(g^{(1)}, r|D)$ by double integration or from $p(g^{(1)}, g^{(2)}, r|D)$ by triple integration. With the joint distribution defined in equation (55) we can now calculate the covariance.

$$COV[d^{(1)}, d^{(2)}|D] = E[(d^{(1)} - E[d^{(1)}|D]) \cdot \quad (56)$$
$$(d^{(2)} - E[d^{(2)}|D])|D]$$
$$= E[d^{(1)} d^{(2)}|D] - E[d^{(1)}|D] \cdot E[d^{(2)}|D] -$$
$$E[d^{(1)}|D] \cdot E[d^{(2)}|D] + E[d^{(1)}|D] \cdot$$
$$E[d^{(2)}|D]$$
$$= E[d^{(1)} d^{(2)}|D] - E[d^{(1)}|D] \cdot$$
$$E[d^{(2)}|D]$$

We can focus on the calculation of the expected value of the product of the delta-Cq values. Therefore we use the same strategy as in the previous section: We integrate over the reference analytically.

$$E[d^{(1)}d^{(2)}|D] = \int\int\int (20 - g^{(1)} + r)(20 - g^{(2)} + r) \cdot \qquad (57)$$

$$p(g^{(1)}, g^{(2)}, r|D)dg^{(1)}dg^{(2)}dr$$

$$= \int\int\int (20 - g^{(1)} + r)(20 - g^{(2)} + r) \cdot$$

$$c^{(1)}c^{(2)}h^{(1)}(g^{(1)})h^{(2)}(g^{(2)}) \cdot$$

$$H(20 - \max\{g^{(1)}, g^{(2)}\} + r - L)$$

$$f(r)dg^{(1)}dg^{(2)}dr$$

$$= c^{(1)}c^{(2)} \cdot \int\int h^{(1)}(g^{(1)})h^{(2)}(g^{(2)}) \cdot$$

$$\int (20 - g^{(1)} + r)(20 - g^{(2)} + r) \cdot$$

$$H(20 - \max\{g^{(1)}, g^{(2)}\} + r - L)$$

$$f(r)drdg^{(1)}dg^{(2)}$$

$$= c^{(1)}c^{(2)} \cdot \int\int h^{(1)}(g^{(1)})h^{(2)}(g^{(2)}) \cdot$$

$$\int_{\max\{g^{(1)},g^{(2)}\}+L-20}^{\infty} (20 - g^{(1)} + r)$$

$$(20 - g^{(2)} + r)f(r)drdg^{(1)}dg^{(2)}$$

Using equations (48) and substituting $g:=\max\{g^{(1)}, g^{(2)}\}$ we can solve the inner integral.

$$E[d^{(1)}d^{(2)} | D] = c^{(1)}c^{(2)} \cdot \int\int h^{(1)}(g^{(1)})h^{(2)}(g^{(2)}) \cdot \qquad (58)$$

$$\left\{ \begin{array}{l} ((20 - g^{(1)} + \mu_r)(20 - g^{(2)} + \mu_r) + \sigma_r^2) \\ \alpha(\max\{g^{(1)}, g^{(2)}\}) + \\ (20 + \mu_r - \min\{g^{(1)}, g^{(2)}\} + L) \\ \beta(\max\{g^{(1)}, g^{(2)}\}) \end{array} \right\} dg^{(1)}dg^{(2)}$$

This equation can be evaluated numerically, the results leads to an estimation of the covariance of two GOIs.

Summary of symbols and abbreviations in this example c special constant for the joint probability of g and r, see equation (31).

$c^{(j)}$ special constant for the joint probability of $g^{(j)}$ and r, see equation (31).

const some constant with respect to all true values d, g, and $r^{(j)}$; may depend on D.

D "data"; abbreviation of all measured values $g_1, \ldots, g_3$, $r_1^{(1)}, \ldots, r_3^{(1)}, r_1^{(2)}, \ldots, r_3^{(2)}, \ldots$ d true delta-Cq value of the GOI $d^{(j)}$ true delta-Cq value of j-th GOI E[.] expected value Erf(.) error function. See equation (45) for definition.

g true raw-Cq value of the GOI $g^{(j)}$ true raw-Cq value of j-th GOI $g_i$ measured raw-Cq value of GOI, i-th replicate $g_i^{(j)}$ measured raw-Cq value of j-th GOI, i-th replicate GOI gene of interest (in contrast to reference gene)

H(.) Heaviside step function: H(x)=0 for x<0, H(x)=1 for x≥0 h(g) help function: proportional to likelihood of all replicates of GOI i index denoting the replicate j index denoting the reference gene L lower bound $\mu_r$ mean of the posterior distribution of true raw-Cq value $N(\mu, \sigma^2)$ normal distribution with mean $\mu$ and variance $\sigma^2$ p(.) probability P(.) probability density r true mean raw-Cq value of reference genes, $r=(r^{(1)}+r^{(2)})/2$ $r^{(j)}$ true raw-Cq value of reference gene j $r_i^{(j)}$ measured raw-Cq value of reference gene j, i-th replicate σ(.) noise model estimating the standard deviation of replicate-to-replicate noise $\sigma_r^2$ variance of the posterior distribution of true raw-Cq value VAR[.] variance υ(.) noise model estimating the probability of "Undetected" End of Example 11

EXAMPLE 12

Calculation of Delta-Cq Value Distributions with Sampled Prior Distribution

Overview

We use the same symbols as in example 11, see above. Delta-Cq values in this example are defined as $$d = \max\{20 - (g - r), L\} \qquad (59)$$

where d is the delta-Cq value, g is the raw-Cq value of the GOI, r is the mean raw-Cq value of the reference genes, and L is the lower bound. Several reference genes are averaged, $$r := \frac{1}{J} \sum_{j=1}^{J} r^{(j)}, \qquad (60)$$

where $r^{(j)}$ is the raw-Cq value of the j-th reference gene and J is the number of reference genes.

The distribution of the true delta-Cq value is estimated from the measurement results using a Bayesian approach: The likelihood is calculated based on a noise model and the prior distribution is sampled from a training set. Technically, the prior distribution is a delta-Cq value distribution which is transformed to a raw-Cq value distribution conditional on the raw-Cq values of the reference genes according to equation (59). The sampling character of the prior is used for an efficient and fast numeric calculation algorithm.

Prior Delta-Cq Value Distribution

Said prior distribution is a distribution of delta-Cq values sampled from some training set. The training set used here is a set of about 300 samples; the same training set was used for other calculations involving additional variables as well.

The prior distribution was constructed by selecting samples from the set of available samples. The selected samples should represent the basic population, thus selection criteria were chosen in a way that did not introduce a bias. On the other hand selection was necessary because not all calculated delta-Cq values have sufficient confidence. This seems like a chicken-and-egg problem: Without a prior distribution we cannot calculate the confidence, without confidence we cannot calculate the prior. We overcame this by evaluating confidence only qualitatively (not quantitatively) using some conservative heuristics. These heuristics may also be applied to other data than the prior distribution training set.

The first selection criterion was that all reference gene replicates had type "Numeric". This excludes samples with no or extremely few total material ("Undetected") as well as "Invalid" measurements.

As discussed in example 1 the confidence of a delta-Cq value is bad only if both, the reference genes and the GOI raw-Cq values are high. We describe this as a heuristic inequality by requiring the uncertainty caused by the lack of information caused by an "Undetected" type measurement result to be completely repaired by the lower bound. This means: We ran 40 PCR cycles, thus the highest possible "Numeric" measurement value is 40. If such a value yields a delta-Cq value equal to the lower bound, then all "Undetected" raw-Cq values with the same reference gene values will also yield a delta-Cq value equal to the lower bound, and thus will be assumed to be sufficiently confident. Mathematically we require $$20-(g-r) \leq L \text{ for } g=40. \tag{61}$$

Substitution and rearrangement yields $$r \leq L+20. \tag{62}$$

This is a simple condition on the reference genes value which can easily be tested based on the reference genes replicates. We refined this criterion by inclusion of a safety zone, because the noise model predicts quite high noise (bad confidence) for raw-Cq values of about 40:

$$r \leq L+20-z, \tag{63}$$

where we chose the safety zone size z between 1 and 5, mainly depending on the size of the training cohort. Please note that the noise model predicts that the noise increases monotonically as a function of the raw-Cq value.

Equation (63) is the second and last inclusion criterion for samples of the prior distribution. Approximately half of the available samples from the training cohort were selected for the prior.

Mean Reference Genes Value Estimation

We first estimate the distribution of the true mean of the reference genes values r according to equation (60) from the measured reference genes values $\{r_i^{(j)}\}$ where i denotes the replicate index and j denotes the reference gene index. All measured reference genes values are required to be either "Numeric" or "Invalid" (we assume outliers within replicates to be eliminated before this processing step).

For a fixed true value $r^{(j)}$ the noise model $\sigma(.)$ we use in this example predicts a measurement value $r_i^{(j)}$ to be normally distributed with standard deviation from the noise model function:

$$r_i^{(j)} | r^{(j)} \propto N(r^{(j)}, \sigma^2(r^{(j)})). \tag{64}$$

Note that $\sigma(.)$ has a different meaning here compared with example 11. In addition, while example 11 uses a Bayesian estimation to determine the true values at this point, we here apply some approximations to avoid too complicated formulas. First, we average the replicates of reference gene j:

$$\bar{r}^{(j)} := \frac{1}{I^{(j)}} \sum_{i=1}^{I^{(j)}} r_i^{(j)}, \tag{65}$$

where $I^{(j)}$ is the number of "Numeric" (non-"Invalid") replicates for reference gene j. We can easily derive a distribution for this average.

$$\bar{r}^{(j)} | r^{(j)} \propto N(r^{(j)}, \sigma^2(r^{(j)})/I^{(j)}) \tag{66}$$

Obviously our average is an unbiased estimator for the true value. Unfortunately its confidence in terms of the variance, $\sigma^2(r^{(j)})/I^{(j)}$, depends on the true value, which is unknown. Since our average $\bar{r}^{(j)}$ already is an estimator for the true value, we use it also for its confidence estimation. Let $s^{(j)}$ be the (estimated) standard deviation of $\bar{r}^{(j)}$, then $$s^{(j)} = \sigma(r^{(j)})/\sqrt{I^{(j)}} \text{ and } STD[r^{(j)}|\bar{r}^{(j)}] \approx s^{(j)}. \tag{67}$$

Under this approximation we estimate the noise by averaging the noise function in the range of the estimated true value.

$$s^{(j)} = E[\sigma(N(\bar{r}^{(j)},(s^{(j)})^2))/\sqrt{I^{(j)}}] \tag{68}$$

This circular equation is solved in $s^{(j)}$ by fix-point iteration. The expected value in equation (68) is calculated based on sample nodes $z_1, \ldots, z_M$ generated from percentiles of the standard normal distribution such that $z_1, \ldots, z_M$ have zero mean and variance equal to 1. Using these sample nodes equation (68) transforms to the fix-point iteration update rule $$s_{i+1}^{(j)} = \frac{1}{M} \sum_{m=1}^{M} \sigma(\bar{r}^{(j)} + (s_i^{(j)}) \cdot z_m)/\sqrt{I^{(j)}} \tag{69}$$

which can be calculated numerically. The starting value is $s_0^{(j)} = \sigma(\bar{r}^{(j)})$, and we set $s^{(j)} = s_i^{(j)}$ after the first iteration i with $|s_{i-1}^{(j)} - s_i^{(j)}| < 10^{-4}$. In the very most cases the fix-point iteration terminates after the first or second iteration since the noise model varies not very much with the raw-Cq value.

In summary, the true reference gene value (conditional on the measurements) is estimated as $$r^{(j)} \propto N(\bar{r}^{(j)},(s^{(j)})^2) \tag{70}$$

and the estimate of the mean of the reference genes values then becomes $$r \propto N\left(\frac{1}{J}\sum_{j=1}^{J} \bar{r}^{(j)}, \frac{1}{J^2}\sum_{j=1}^{J}(s^{(j)})^2\right). \tag{71}$$

Since we use these calculation results below we assign variable names to them. Define $$\mu_r := \frac{1}{J}\sum_{j=1}^{J} \bar{r}^{(j)} \text{ and } \sigma_r^2 := \frac{1}{J^2}\sum_{j=1}^{J}(s^{(j)})^2, \tag{72}$$

thus we have the $r \propto N(\mu_r, \sigma_r^2)$.

Delta-Cq Value Calculation: General Case

In opposite to the reference genes measurements the GOI measurements are allowed to result in "Undetected". "Undetected" in this example means that the true raw-Cq value is above 40 (the number of PCR cycles run here) with high probability. Since in this case the true value cannot be well described by a normal distribution we use a Bayesian approach for the estimation.

The true delta-Cq value is estimated from the GOI replicate measurement values $g_1, \ldots, g_I$ and the true mean value of the reference genes r. Similar to the reference genes measurements "Invalid" measurements contain no information and are removed first; thus, $g_1, \ldots, g_I$ are of type "Numeric" or "Undetected" only. We use the Bayesian equation conditional on the reference to calculate the posterior distribution of the true delta-Cq value.

$$p(d \mid g_1, \ldots, g_I, r) = \frac{p(d \mid r) p(g_1, \ldots, g_I \mid d, r)}{p(g_1, \ldots, g_I \mid r)} \quad (73)$$

We discuss the terms on the right hand side separately. The prior distribution is modeled to be independent of the reference, $p(d \mid r) = p(d)$, and then the prior distribution samples from the training set as discussed above are used. Please note that by using this prior delta-Cq values below the lower bound L have zero probability in the prior, and thus also have zero probability in the posterior.

The likelihood in equation (73) can be divided into factors for the separate measurements since they are independent observations. Moreover the conditions d and r can be summarized into one variable only, g, based on the definition of delta-Cq values: $g = 20 - d + r$. Please note that due to the prior we do not have to consider delta-Cq values below the lower bound here.

The denominator in equation (73) does not depend on the delta-Cq value and thus is abbreviated as a constant that is determined later by normalizing the posterior distribution. So far we have $$p(d \mid g_1, \ldots, g_I, r) = const \cdot p(d) \cdot \prod_{i=1}^{I} p(g_i \mid g). \quad (74)$$

The replicate likelihood factors have different forms according to the type of measurement. As already discussed with the application for references, for "Numeric" replicates the measured raw-Cq value is modeled by a normal distribution using the noise model.

$$p(g_i \mid g) = const \cdot \frac{1}{\sigma(g)} \exp\left(-\frac{(g_i - g)^2}{2\sigma^2(g)}\right) \quad (75)$$

"Undetected" replicates represent a raw-Cq value above 40, therefore we use the cumulated normal distribution function $\Phi(.)$ for the likelihood.

$$p(g_i = \text{"Undected"} \mid g) = const \cdot \Phi\left(\frac{g - 40}{\sigma(40)}\right) \quad (76)$$

Please note that variable g within the right sides of equations (75) and (76) is directly connected to the delta-Cq value d via its definition since the reference r is fixed.

Substituting equations (75) and (76) into (74) enables us to calculate a posterior distribution for the delta-Cq value. Since the prior is based on sample nodes the posterior is a distribution over these finite-numbered sample nodes. Let $d_1, \ldots, d_K$ be the prior sample nodes. The prior distribution assigns equal probability to each of them. The posterior is calculated by $$P(d_k \mid g_1, \ldots, g_I, r) = \quad (77)$$

$$const \cdot \prod_{i=1}^{I} \begin{cases} \frac{1}{\sigma(g_k)} \exp\left(-\frac{(g_i - g_k)^2}{2\sigma^2(g_k)}\right) & : g_i \text{ is "Numeric"} \\ \Phi\left(\frac{g_k - 40}{\sigma(40)}\right) & : g_i \text{ is "Undected"}. \end{cases}$$

Please note that on the right hand side of this equation variable $g_k$ is calculated by $g_k = 20 - d_k + r$. The constant term is different from that of equation (74), is independent of the sample node index k and is determined by normalization, i.e. solution of $$\sum_{k=1}^{K} P(d_k \mid g_1, \ldots, g_I, r) = 1. \quad (78)$$

The posterior distribution of the delta-Cq values now is described in terms of the prior sample nodes and their probability. In the next step of processing this description of a distribution is changed to an alternative one: The distribution is now described by a set of sample nodes $\tilde{d}_1, \ldots, \tilde{d}_M$ having equal probability but describing (approximately) the same distribution. The mapping is done by linear interpolation of the cumulated probability. There are two advantages of the new distribution description: First, the number of sample nodes M can be chosen much smaller since we do not need to describe many sample nodes with negligible probability; this saves memory storage as well as computation time in the next processing steps. Second, the number of sample nodes M can be chosen independently of the GOI while the number of prior sample nodes K depends on the gene. This enables us to store the results for several genes in a matrix instead of vectors of different length for each gene.

So far we have calculated the posterior distribution conditional on the true reference value r. Since we do not know r exactly we have to include the estimated variance of it into our delta-Cq value distribution. Therefore, as the next processing step, we apply an approximate adjustment to our distribution sample nodes. The m-th adjusted sample node $d_m'$ will be $$d_m' = \tilde{d}_m + \alpha z_m, \quad (79)$$

where $\alpha$ is the adjustment size factor and $z_m$ is a percentile of the standard normal distribution as introduced above with application to the reference gene value estimation. Please note that $\tilde{d}_1, \ldots, \tilde{d}_M$ as well as $z_1, \ldots, z_M$ are in ascending order. The adjustment size factor $\alpha$ is determined by requiring the adjusted variance to include the reference estimation variance, i.e.

$$\text{VAR}[d_1', \ldots, d_M'] = \text{VAR}[\tilde{d}_1, \ldots, \tilde{d}_M] + \sigma_r^2. \quad (80)$$

Remember that $\sigma_r$ is the standard deviation of the estimated mean of the reference genes values, and that the GOI estimations $\tilde{d}_1, \ldots, \tilde{d}_M$ are independent of the reference measurements. Calculating the variance on both sides of equation (79) yields $$\text{VAR}[d_1', \ldots, d_M'] = \text{VAR}[\tilde{d}_1, \ldots, \tilde{d}_M] + \alpha^2 + 2\alpha \text{COV}[\tilde{d}_1, \ldots, \tilde{d}_M; z_1, \ldots, z_M]. \quad (81)$$

This can be combined with equation (80) and solved in $\alpha$.

$$\alpha = -\text{COV}[\tilde{d}_1, \ldots, \tilde{d}_M; z_1, \ldots, z_M] + \sqrt{\text{COV}[\tilde{d}_1, \ldots, \tilde{d}_M; z_1, \ldots, z_M] + \sigma_r^2} \quad (82)$$

Now we can calculate the adjusted delta-Cq values.
The last processing step is to apply the lower bound again.

$$d_m'' := \max\{d_m', L\} \quad (83)$$

Sample nodes $d_1'', \ldots, d_M''$ are the final estimated distribution for the delta-Cq values. In an application one may calculate the mean and standard deviation from them to use as estimate with confidence.

Delta-Cq Value Calculation: Normal Distribution Case

The general case using a Bayesian estimation as described above is quite time-consuming and its results (mean of final distribution) slightly deviate from a direct calculation, i.e. averaging "Numeric" replicates and then calculating the delta-Cq value by its definition d=20−(g−r). Therefore we describe an alternative calculation scheme here which can be used if no "Undetected" replicate is present. Most parts of this calculation have already been discussed above. First, we apply the procedure used for the reference genes value estimation to our GOI: let the results be called $\mu_g$ (instead of $\mu_r$) for the mean and $\sigma_g$ (instead of $\sigma_r$) for the standard deviation. The true raw-Cq value of the GOI is then estimated as $g \propto N(\mu_g, \sigma_g^2)$. The delta-Cq value then is estimated as $$g \propto N(20-\mu_g+\mu_r, \sigma_g^2+\sigma_r^2). \tag{84}$$

To produce a compatible data format we describe this distribution by sample nodes $d_1', \ldots, d_M'$ with equal weight; thus we define $$d_m' := 20-\mu_g+\mu_r+z_m(\sigma_g^2+\sigma_r^2). \tag{85}$$

The last step of calculation is the application of the lower bound according to equation (83).

Matlab-Code of Implementation

We complete this example by showing some Matlab® (The Math-Works, Inc., Version 2009b) script code that calculates a delta-Cq value distribution from GOI and reference genes replicates. In addition to the text above it contains some ideas to improve numerical behavior and to speed-up the implementation.

```
function deltaCq = CalculateDeltaCq(replGoi, replRef, ...
                                    prior, numCycles)
% parameters:
%   replGoi: I * 1 double matrix. Measurement values of I
%       replicate measurements of the GOI. Coding: NaN
%       represents "Invalid", inf represents "Undetected".
%   replRef: I * J double matrix. Measurement values of I
%       replicate measurements of J reference genes.
%       Coding: same as replGoi.
%   prior: K * 1 double matrix. Delta-Cq prior values. Must be
%       sorted ascendingly, prior(1) contains the lower bound.
%   numCycles: 1 * 1 double. Number of PCR cycles run, i.e. the
%       highest possible "Numeric" value. In this example we
%       used numCycles=40.
% returns:
%   deltaCq: M * 1 double matrix. Samples nodes representing the
%       delta-Cq value distribution.
% Outliers are assumed to be already set to NaN at this point.
% pre-allocate return
NUM_NODES = 50;
NORMAL_NODES =
    norminv((0.5:1:NUM_NODES-0.5)'/NUM_NODES);
NORMAL_NODES = NORMAL_NODES / std(NORMAL_NODES);
% calculate reference genes estimate
numRefGenes = size (replRef, 2);
muRef = 0;                    % mean estimate
sigma2Ref = 0;                % variance estimate
for k = 1:numRefGenes
    [m, s] = noiseEstimate(replRef(:, k), NORMAL_NODES);
    muRef = muRef + m;
    sigma2Ref = sigma2Ref + s^2;
end
muRef = muRef / numRefGenes;
sigma2Ref = sigma2Ref / numRefGenes^2;
% no delta-Cq value if reference contains "Undetected":
if ~isfinite(muRef), deltaCq = NaN; end
% calculate delta-Cq value
if all(isnan(replGoi))
    % all replicates are "Invalid"
    deltaCq = NaN;
elseif ~any(replGoi == inf)
    % no "Undetected": normal distribution case
    [m, s] = noiseEstimate (replGoi, NORMAL_NODES);
    deltaCq = 20 - m + muRef + NORMAL_NODES * sqrt(s^2 +
        sigma2Ref);
else
    % general case: Bayesian estimation
    deltaCq = 20 + muRef - bayesEstimate( ...
        replGoi, 20 - prior + muRef, numCycles, NUM_NODES) ;
    % adjust samples nodes, increase variance by sigma2Ref
    c = cov(deltaCq, NORMAL_NODES) ; c = c(1, 2);
    deltaCq = deltaCq + NORMAL_NODES * (-c + sqrt(c^2 +
        sigma2Ref));
end
% apply lower bound
deltaCq(deltaCq < prior(1)) = prior(1);
end
function [m, s] = noiseEstimate (repl, NORMAL_NODES)
m = nanmean(repl);
s = NoiseModel(m) / sqrt(sum(~isnan(repl)));
sOld = inf;
while (sOld - s) >= 1E-4% fix-point iteration
    sOld = s;
    rawCq = NORMAL_NODES * s + m;
    s = mean(NoiseModel(rawCq)) / sqrt(sum(~isnan(repl)));
end
end
function nodes = bayesEstimate(replGoi, rawPrior, ...
                               numCycles, NUM_NODES)
% get estimated noise
s = NoiseModel(rawPrior);
% calculate posterior
postPvalues = ones(size(rawPrior));
for k = 1:length(replGoi)
    if isnan(replGoi(k))
        % "Invalid"
        continue
    elseif replGoi(k) == inf
        % "Undetected"
        fac = normcdf((rawPrior - numCycles) ./ s);
        if all(fac <= 1E-50)
            % all rawPriors are very small: avoid floating point
            % underflow, select most probable rawPrior only
            fac = (rawPrior == max(rawPrior));
        end
    else
        % "Numeric"
        fac = 1 ./ s .* exp(-((replGoi(k) - rawPrior) ./ s).^2 / 2);
    end
    postPvalues = postPvalues .* fac;
    % normalize in each iteration due to numeric robustness:
    postPvalues = postPvalues / sum(postPvalues);
end
% convert posterior distribution to alterantive description
P = cumsum([0; postPvalues; 0]);
nodes = NaN (NUM_NODES, 1); % memory pre-allocation
for i = 1:NUM_NODES
    p0 = (i-1) / NUM_NODES;   % cumulated probability before new
                                node
    p1 = i / NUM_NODES;       % cumulated probability after new
                                node
    idx = find(P(2:end-1) >= p0 & P(1:end-2) <= p1); % old nodes
    wgt = [P(idx(2:end)); p1] - [p0; P(idx(2:end))]; % interpolation
    % here we have: sum(wgt) approx. 1/NUM_NODES
    nodes(i) = sum(wgt .* rawPrior(idx)) / sum(wgt);
end
end
function sigma = NoiseModel(rawCq)
% returns standard deviation of replicate noise
rawCq = min(rawCq, 40);
sigma = log2( 2^0.3 + 2.^((rawCq - 35) / 2) );
end
```

End of Example 12

EXAMPLE 13

Calculation of delta-delta-Cq value distributions Livak and Schmittgen, [1], and Pfaffl, [2], describe a method for comparing or compensating delta-Cq values with a reference sample, the so-called delta-delta-Cq method. Let $d_1$ be the delta-Cq value for the sample of interest and $d_2$ be the delta-Cq value for the reference sample, the delta-delta-Cq value $\delta$ is defined as $$\delta = d_1 - d_2. \tag{86}$$

Delta-Cq values $d_1$ and $d_2$ may be calculated according to any of the above examples. With these estimates an estimate for the delta-delta-Cq value can easily be derived, because $d_1$ and $d_2$ are independent. If the estimation of the true value of $d_1$ and $d_2$ is calculated as a general distribution, the corresponding delta-delta-Cq value distribution can be calcufated by convolution according to equation (86). If the true values of $d_1$ and $d_2$ are described by an expected value and a variation only, these features can be calculated for the delta-delta-Cq value, too:

$$E[\delta] = E[d_1] - E[d_2]$$

$$VAR[\delta] = VAR[d_1] + VAR[d_2]. \tag{87}$$

EXAMPLE 14

Considering Primer Efficiencies

The delta-Cq method assumes GOI and reference genes to have equal efficiency: Diluting the sample will raise both Cq values by the same amount and leaves the delta-Cq value unchanged.

Removing this assumption introduces constant factors for the raw-Cq values:

$$d = 20 - (c_g \cdot g - c_r \cdot r), \tag{88}$$

where $d$ is the efficiency-compensated delta-Cq value, $g$ is the raw-Cq value of the GOI, $r$ is the raw-Cq value of the reference gene and $c_g$ and $c_r$ are constants compensating for non-ideal efficiencies. Constants $c_g$ and $c_r$ do not depend on the sample nor measured values associated with it; they may depend on the reagent lots or other technical parameters of the measuring process. The noise model may or may not consider the efficiency compensation. Nevertheless, for a chosen noise model and fixed constants $c_g$ and $c_r$ the skilled person can easily derive the delta-Cq value estimate including confidence information similar to any of the above examples.

EXAMPLE 15

Usage and Application of Claimed Method

From a breast cancer tumor removed during surgery tissue slides are cut, RNA is extracted and the expression levels of several genes are measured by quantitative PCR. The resulting raw-Cq values are processed by a calculation method that is claimed by this patent application and that calculates delta-Cq value estimates in term of a mean and a variance for each GOI. More precise, let K be the number of GOIs (K=1 for a normalized, single gene assay; K≥2 for multi-index assays), let $m_1, \ldots, m_K$ be the estimated delta-Cq values, and let $s_1, \ldots, s_K$ contain the corresponding confidence information in terms of the standard deviations.

The method assumes an approximate normal distribution of the true delta-Cq values $d_1, \ldots, d_K$:

$$d_k \propto N(m_k, s_k^2). \tag{89}$$

Furthermore, let $$q = \sum_{k=1}^{K} c_k \cdot d_k, \tag{90}$$

where q is a score that predicts the probability of the patient to develop a metastasis, and $c_1, \ldots, c_K$ are some constant coefficients. An estimation of the score can be calculated from the estimations of the delta-Cq values:

$$q \propto N\left(\underbrace{\sum_{k=1}^{K} c_k \cdot m_k}_{\mu}, \underbrace{\sum_{k=1}^{K} c_k^2 \cdot s_k^2}_{\sigma^2}\right). \tag{91}$$

Based on these results one can define confidence intervals for the score, i.e. $[\mu - 1.96\sigma, \mu + 1.96\sigma]$. In addition, if only the estimated score $\mu$ shall be reported to the patient or physician, one may define a quality rule: If $\sigma \leq \sigma_{max}$ for some constant $\sigma_{max}$ the score is reported, otherwise the measurements have to be repeated.

Another application comes into play when a threshold $\theta$ is applied to the score. The physician may select a different or more intense treatment if $q > \theta$. To decide whether the score is above or below the threshold the corresponding probability can be calculated from the cumulative normal distribution function.

$$P(q \leq \theta) = \Phi\left(\frac{\mu - \theta}{\sigma}\right) \tag{92}$$

The application of a threshold to a fixed score may in particular apply to some special, single genes (K=1): ESR1, PGR, ERBB2, KI67 and other proliferation-related genes.

Comparison to state of the art:

Bengtsson et al, [3], present a detailed noise model considering different sources of measurement noise during concerning the RT-PCR: pure PCR noise, dilution noise, RT-step noise and biological noise. These sources with the exception of the pure PCR noise can be seen as possible extensions to the present invention. [3] does not consider delta-Cq values.

Livak and Schmittgen, [1], describe the so-called delta-delta-Ct method: It extends the delta-Ct method described in this patent application by comparing the sample to measure with a reference sample. The reference sample may be tissue from a different organ or tissue from a differently treated animal. In addition the described method considers different amplification efficiencies of the GOI as well as the reference gene.

The authors do not discuss confidences for delta-Ct nor delta-delta-Ct values. No noise model is discussed. The skilled person can easily combine the definition of delta-delta-Ct values with this patent application: E.g. similar to the derivation of equations describing the distribution of delta-Cq values as shown in examples 10, 11 and 12, the skilled person can derive corresponding equations for delta-delta-Ct values.

Pfaffl, [2], describes a similar mathematical approach as [1], but uses a calibrator sample as reference. Again, confideuces for raw measurement values nor calculated results are discussed, no noise model is applied. The skilled person can easily combine the approach with this patent application.

We think that confidences for individual test results are not calculated up to now. Instead of this the total RNA amount or the reference material amount is controlled which means that samples with small of said amount are rejected. The disadvantage of this method is that more samples than necessary are rejected, in particular in cohorts with small tissue samples and/or long storage time (i.e. training and validation cohorts). The disadvantages are (i) increased costs and processing time for the unnecessarily rejected samples, and (ii) worse confidence and potential biases due to reduced sample sizes in training and validation cohorts.

Controlling test results individually by confidence calculations is superior to controlling them only statistically in general.

LITERATURE

[1] Livak K J, Schmittgen T D (2001). Analysis of relative gene expression data using real-time quantitative PCR and the 2^[−delta delta Ct] method. Methods 25, 402-408.
[2] Pfaffl M W (2001). A new mathematical model for relative quantification in real-time RT-PCR. Nucleic Acids Research 29, e45
[3] Bengtsson M, Hemberg M, Rorsman P, Stahlberg A (2008). Quantification of mRNA in single cells and modelling of RT-qPCR induced noise. Additional file 2: Mathematical Models of RT-qPCR Noise.
[4] Bustin S A, Benes V, Garson J A, Hellemans J, Huggett J, Kubista M, Mueller R, Nolan T, Pfaffl M W, Shipley G L, Vandesompele J, Wittwer C T (2009). The MIQE Guidelines: Minimum Information for Publication of Quantitative Real-Time PCR Experiments. Clinical Chemistry 55, 611-622.

The invention claimed is:

1. A method for determining a quality control criterion for a target raw-Cq value of a target analyte obtained from quantitative polymerase chain reaction (PCR) measurements, the method comprising:
    determining, by a processor of a computing device, a target raw-Cq value from quantitative PCR measurements, the target raw-Cq value being representative of a concentration or activity of a target analyte from a first sample;
    determining by the processor, a reference raw-Cq value from quantitative PCR measurements, the reference raw-Cq value being representative of a concentration or activity of a reference analyte from at least one of (i) the first sample, and (ii) one or more other samples;
    calculating, by the processor, an unbounded delta-Cq value and respective confidence information based on a calculated difference between the target raw-Cq value and the reference raw-Cq value;
    calculating, by the processor, a bounded delta-Cq value and respective confidence information, wherein the bounded delta-Cq value is bounded by applying an upper bound, a lower bound, or both, the confidence information corresponding to the bounded delta-Cq value being used to determine a quality control criterion for the target raw-Cq value of the target analyte; and
    using the quality control criterion to perform a quality control action.

2. The method of claim 1, wherein the applying of the upper bound, lower bound or both, generates a variance of the bounded delta-Cq value which is smaller than a variance of the unbounded delta-Cq value, for at least one observable Cq value.

3. The method of claim 1, wherein the target analyte is a nucleic acid selected from the group consisting of DNA, RNA, or mRNA.

4. The method of claim 1, wherein the target raw-Cq value and the reference raw-Cq value comprise threshold cycle (cT) values.

5. The method of claim 1, wherein each of the target raw-Cq and the reference raw-Cq measurement values comprise one of:
    (i) a numeric value representative of the concentration or activity of the target analyte or the reference analyte, respectively;
    (ii) an "Undetected" value representative of a concentration or activity below a limit of detection (LOD) of the target analyte or the reference analyte, respectively; or
    (iii) an "Invalid" value indicating the occurrence of a severe problem during measurement and/or that the measurement value should be ignored.

6. The method of claim 1, further comprising:
    measuring, by the processor, one or more replicates for each of the target analyte and/or the reference analyte; and
    combining, by the processor, the one or more replicates of each of the target analyte and/or the reference analyte into each of the unbounded and/or bounded delta-Cq values.

7. The method of claim 6, further comprising:
    eliminating, by the processor, outliers within the one or more replicates using an automated procedure before determining the target raw-Cq value.

8. The method of claim 1, wherein the lower bound is determined based on a training data set by constrained optimization,
    wherein the lower bound is optimized to be as high as possible to make a variance of bounded normalized values as small as possible,
    wherein a constraint depends on an application of normalized values, and
    wherein the lower bound is constrained to be sufficiently low such that for said application, no distinction between values at and below the lower bound needs to be made.

9. The method of claim 1, wherein the calculating of the unbounded delta-Cq value and respective confidence information is based on a noise model, and
    wherein a true value is modeled as a normal distribution with a mean equal to one of the measured raw-Cq values and a standard deviation calculated from a parameterized function comprising parameters fitted based on training data.

10. The method of claim 1, wherein the calculating of the unbounded delta-Cq value and respective confidence information is based on a noise model, and
    wherein a measured value is modeled as a normal distribution with a mean equal to a true value and a standard deviation calculated from a parameterized function comprising parameters fitted based on training data.

11. The method of claim 5, wherein, in the event that one of the target raw-Cq and the reference raw-Cq values comprises an "Undetected" value, a noise model assigns a fixed distribution to a true value, said fixed distribution having a finite or an infinite expected value, a finite or an infinite variance, or a bounded, half-bounded or unbounded support.

12. The method of claim 5, wherein the quality control action comprises at least one of the following:
(i) report or reject the one or more of the unbounded and/or bounded target raw-Cq values;
(ii) repeat or not repeat measurements of the target raw-Cq value and the reference raw-Cq value;
(iii) decide whether the one or more of the unbounded and/or bounded target raw-Cq values are used for a decision; or
(iv) determine whether the one or more of the unbounded and/or bounded target raw-Cq values and/or a combination thereof exceeds a threshold.

13. The method of claim 1, wherein the upper bound is determined based on a training data set by constrained optimization,
wherein the upper bound is optimized to be as low as possible to make a variance of bounded normalized values as small as possible,
wherein a constraint depends on an application of normalized values, and
wherein the upper bound is constrained to be sufficiently high such that for said application, no distinction between values at and above the upper bound needs to be made.

14. The method of claim 1, wherein the unbounded and bounded delta-Cq values are (i) normalized values, or (ii) estimated values calculated using an estimator.

15. The method of claim 1, wherein the reference raw-Cq value is a mean of the PCR measurement of the reference analyte from each of the at least one of (i) the first sample, or (ii) the one or more other samples, and
wherein the calculating the unbounded delta-Cq value and the bounded delta-Cq value comprises calculating the difference between a predetermined constant and the calculated difference between the target raw-Cq value and the reference raw-Cq value.

16. A system for determining a quality control criterion for a target raw-Cq value of a target analyte obtained from quantitative polymerase chain reaction (PCR) measurements, comprising:
memory storing instructions that are executable to perform operations comprising:
determining a target raw-Cq value from quantitative PCR measurements, the target raw-Cq value being representative of the concentration or activity of a target analyte from a first sample;
determining a reference raw-Cq value from quantitative PCR measurements, the reference raw-Cq value being representative of the concentration or activity of a reference analyte from at least one of (i) the first sample, and (ii) one or more other samples;
calculating an unbounded delta-Cq value and respective confidence information based on the target raw-Cq value and the reference raw-Cq value;
calculating a bounded delta-Cq value and respective confidence information, wherein the bounded delta-Cq value is bounded by applying an upper bound, a lower bound, or both, the confidence information corresponding to the bounded delta-Cq value being used to determine a quality control criterion for the target raw-Cq value of the target analyte; and
using the quality control criterion to perform a quality control action.

17. The system of claim 16, wherein the applying of the upper bound, lower bound or both, generates a variance of the bounded delta-Cq value which is smaller than a variance of the unbounded delta-Cq value, for at least one observable Cq value.

18. The system of claim 16, wherein the target analyte is a nucleic acid selected from the group consisting of DNA, RNA, or mRNA.

19. The system of claim 16, wherein the target raw-Cq value and the reference raw-Cq value comprise threshold cycle (cT) values.

20. The system of claim 16, wherein each of the target raw-Cq and the reference raw-Cq measurement values comprise one of:
(i) a numeric value representative of the concentration or activity of the target analyte or the reference analyte, respectively;
(ii) an "Undetected" value representative of a concentration or activity below a limit of detection (LOD) of the target analyte or the reference analyte, respectively; and
(iii) an "Invalid" value indicating the occurrence of a severe problem during measurement and/or that the measurement value should be ignored.

21. The system of claim 16, wherein the quality control action comprises at least one of the following:
(i) report or reject the one or more of the unbounded and/or bounded target raw-Cq values;
(ii) repeat or not repeat measurements of the target raw-Cq value and the reference raw-Cq value;
(iii) decide whether the one or more of the unbounded and/or bounded target raw-Cq values are used for a decision; or
(iv) determine whether the one or more of the unbounded and/or bounded target raw-Cq values and/or a combination thereof exceeds a threshold.

* * * * *